US011739035B2

(12) United States Patent
Coupan et al.

(10) Patent No.: US 11,739,035 B2
(45) Date of Patent: Aug. 29, 2023

(54) GAS TO OLEFINS PROCESSES WITH COPRODUCTION OF HYDROGEN

(71) Applicants: TOTALENERGIES ONETECH, Courbevoie (FR); SULZER MANAGEMENT AG, Winterthur (CH)

(72) Inventors: Romuald Coupan, Vanves (FR); Nikolai Nesterenko, Nivelles (BE); Gleb Veryasov, Nivelles (BE)

( * ) Notice: Subject to any disclaimer, the term of this patent is extended or adjusted under 35 U.S.C. 154(b) by 0 days.

(21) Appl. No.: 17/915,945

(22) PCT Filed: Mar. 29, 2021

(86) PCT No.: PCT/EP2021/058143
§ 371 (c)(1),
(2) Date: Sep. 29, 2022

(87) PCT Pub. No.: WO2021/198172
PCT Pub. Date: Oct. 7, 2021

(65) Prior Publication Data
US 2023/0150901 A1    May 18, 2023

(30) Foreign Application Priority Data
Mar. 30, 2020   (EP) ..................................... 20315077

(51) Int. Cl.
*C07C 17/10* (2006.01)
*C25B 1/24* (2021.01)
(Continued)

(52) U.S. Cl.
CPC .............. *C07C 17/10* (2013.01); *C01B 7/093* (2013.01); *C01B 32/05* (2017.08); *C07C 4/06* (2013.01);
(Continued)

(58) Field of Classification Search
CPC ........ C07C 17/10; C07C 4/06; C07C 2429/04; C25B 1/24; C25B 1/02; C01B 7/093; C01B 32/05
See application file for complete search history.

(56) References Cited

U.S. PATENT DOCUMENTS

| 2009/0308759 A1 | 12/2009 | Waycuilis |
| 2010/0087686 A1 | 4/2010 | Fong et al. |

FOREIGN PATENT DOCUMENTS

| EP | 0921176 A1 | 6/1999 |
| GB | 2571248 A | 8/2019 |
| WO | 2010/009376 A1 | 1/2010 |

OTHER PUBLICATIONS

Search Report dated Jun. 4, 2021 issued in corresponding International Application No. PCT/EP2021/058143.
(Continued)

*Primary Examiner* — Jafar F Parsa
(74) *Attorney, Agent, or Firm* — Nath, Goldberg & Meyer; Joshua B. Goldberg

(57) ABSTRACT

The present disclosure relates in its first aspect to a process of converting a stream comprising methane into chemicals, said process being remarkable in that it comprises the steps of providing a first stream (1, 5, 11) comprising methane, providing a second stream (79) which is a bromine-rich stream, putting into contact said first stream (15) with said second stream (79) to obtain a third stream (21) comprising at least unreacted methane, methyl bromide, dibromomethane, and hydrogen bromide and removing said dibromomethane from said third stream (21), to produce a dibromomethane stream (103) and a fourth stream (27) comprising unreacted methane, methyl bromide and hydrogen bromide; wherein the fourth stream (27) is converted into chemicals. In its second aspect, the present disclosure
(Continued)

concerns an installation for carrying out the process of the first aspect.

18 Claims, 4 Drawing Sheets

(51) Int. Cl.
    *C25B 1/02*     (2006.01)
    *C01B 7/09*     (2006.01)
    *C07C 4/06*     (2006.01)
    *C01B 32/05*     (2017.01)

(52) U.S. Cl.
    CPC ................. *C25B 1/02* (2013.01); *C25B 1/24* (2013.01); *C07C 2529/04* (2013.01)

(56) References Cited

OTHER PUBLICATIONS

Written Opinion dated Jun. 4, 2021 issued in corresponding International Application No. PCT/EP2021/058143.
Direct/Information comments regarding search in priority application No. EP 20315077.6 dated Mar. 29, 2021.

GAS TO OLEFINS PROCESSES WITH COPRODUCTION OF HYDROGEN

This is a National Phase Application filed under 35 U.S.C. 371 as a national stage of PCT/EP2021/058143, filed Mar. 29, 2021, an application claiming the benefit of European Application No. 20315077.6, filed Mar. 30, 2020, the content of each of which is hereby incorporated by reference in its entirety.

FIELD OF THE DISCLOSURE

The present disclosure relates to gas to olefins processes.

TECHNICAL BACKGROUND

Natural gas is an available fossil resource mainly composed of light alkanes. The valorisation of natural gas as feedstock for petrochemical industry is of interest as natural gas is cheap at source. Accordingly, the conversion of light alkanes into products like syngas, methanol, olefins or aromatics is highly valuable.

Oxygen-based processes are the current practices for natural gas conversion. However, processes involving the presence of oxygen leads unavoidably to the formation of carbon dioxide and water in the final product streams. The carbon efficiency of any processes contacting alkanes and oxygen does not exceed 75%.

Recently, technology like the Gas-to-Aromatics (G2A) technology from GTC Technologies based on bromine mediated activation of methane, was presented. The G2A process aims at converting methane to liquid hydrocarbons i.e. C6-C9 aromatics, C5 and C10+ products. In such a process, hydrogen bromide by-product of activation is recycled back to bromine consuming oxygen and coproducing water. This first-generation technology thus offers a low carbon way to transform methane to chemicals and water with high carbon efficiency of about 85%. Current G2A technology is nevertheless not an oxygen-free process as oxygen is used for bromine recovery and produce water.

The reforming process is the most practical current commercial process i.e. Steam Methane Reforming (SMR), Auto-Thermal Reforming (ATR), Dry Methane Reforming (DMR), Partial Oxidation Reforming (PDX).

The process of reforming of methane (SMR, ATR, DMR, PDX) is exemplified by the following chemical equations.

SMR: $CH_4 + H_2O \rightarrow CO + 3H_2$

ATR/PDX: $2CH_4 + O_2 \rightarrow 2CO + 4H_2$

DMR: $CH_4 + CO_2 \rightarrow 2CO + 2H_2$

Methane reforming process produces synthesis gas (i.e. a mixture of carbon monoxide and hydrogen) that can be further converts to liquid hydrocarbons in Gas-to-Liquid process (GTL) or to methanol in Gas-to-Methanol process (GTM), as indicated in the following two chemical equations:

GTL: $nCO + (2n+1)H_2 \rightarrow C_nH_{2n+2} + nH_2O$

GTM: $CO + 2H_2 \rightarrow CH_3OH$

Also, methanol can be used as feedstock in processes such as Methanol-to-Gasoline (MTG), Methanol-to-Olefins (MTO), and Methanol-to-Propylene (MTP).

The conversion of methanol (MTG, MTO, MTP) can be summarized by the following chemical equation.

$nCH_3OH \rightarrow C_nH_{2n+n}H_2O$

In recent times, the Oxidative Coupling of Methane (OCM) was developed. It consists of a direct catalytic oxygen-based process to convert methane into ethylene as shown in the following chemical equation:

$2CH_4 + O_2 \rightarrow C_2H_4 + 2H_2O$

All oxidative conversion processes imply the formation of carbon dioxide and water in the final product streams.

$CH_4 + 2O_2 \rightarrow CO_2 + 2H_2O$

The issue with the formation of carbon dioxide and water is then their further transformation into valuable chemicals, such as the conversion of water into hydrogen and the reaction of the hydrogen with the carbon dioxide to form various useful chemical is highly demanding in energy. There is thus a need for reactivation of these compounds at low energy costs.

In particular, US2006/0100469 describes a process for converting gaseous alkanes to olefins and liquid hydrocarbons wherein a gaseous feed containing alkanes is reacted with a dry bromine vapour to form alkyl bromides and hydrobromic acid vapour. The mixture of alkyl bromides and hydrobromic acid are then reacted over a synthetic crystalline alumino-silicate catalyst, such as an X or Y type zeolite, at a temperature of from about 250° C. to about 500° C. to form olefins, higher molecular weight hydrocarbons, hydrobromic acid vapour and coke.

WO2009/152403 describes a process for converting gaseous alkanes to olefins, higher molecular weight hydrocarbons or mixtures thereof wherein a gaseous feed containing alkanes is thermally reacted with a dry bromine vapour to form alkyl bromides and hydrogen bromide. Poly-brominated alkanes present in the alkyl bromides are further reacted with methane over a suitable catalyst to form monobrominated species. The mixture of alkyl bromides and hydrogen bromide is then reacted over a suitable catalyst at a temperature sufficient to form olefins, higher molecular weight hydrocarbons or mixtures thereof and hydrogen bromide. The catalyst may suffer from coke deactivation, depending on the reaction condition involved.

WO2008/143940 describes an improved continuous process for converting methane, natural gas, and other hydrocarbon feedstocks into one or more higher hydrocarbons, methanol, amines, or other products which comprises continuously cycling through hydrocarbon halogenation, product formation, product separation, notably from coke, and electrolytic regeneration of halogen combined with hydrogen production.

WO 2010/009376 relates to a continuous process for converting natural gas to liquid hydrocarbons via bromination of natural gas. Hydrogen bromide is formed, and separated from the liquid hydrocarbons by aqueous extraction and combination of a liquid-liquid splitter.

US 2010/0087686 relates to an integrated process for producing aromatic hydrocarbons and ethylene and/or propylene from low molecular weight hydrocarbons, such as methane, via activation of the low molecular weight hydrocarbons by bromination. Any hydrogen bromide which is formed is separated by aqueous extraction.

US2009/0308759 describes a process of activation of natural gas by bromination. The brominated products are thus converted by catalysis into C2+ hydrocarbons. During this process, it is important to control the temperature to control the rate of deactivation of the catalysis because, during the conversion into C2+ hydrocarbons, the formation of carbonaceous coke is observed. The formation of the coke has an impact on the stability of the catalyst, which must be regenerated when a drop in the conversion is observed.

As the olefins market is still continuously growing, there is a need for competitive olefins-producing processes. However, the above-described processes cannot be relied on in term of catalyst stability due to the by-side of coke.

There is, therefore, a need for a gas to olefins process that does not suffer from catalytical deactivation.

SUMMARY OF THE DISCLOSURE

According to a first aspect, the disclosure provides a process for converting a stream comprising methane into chemicals, said process being remarkable in that it comprises the following steps:
  a) providing a first stream comprising methane ($CH_4$);
  b) providing a second stream which is a bromine ($Br_2$)-rich stream;
  c) putting into contact said first stream with said second stream under bromination reaction conditions to obtain a third stream comprising at least unreacted methane, methyl bromide ($CH_3Br$), dibromomethane ($CH_2Br_2$), and hydrogen bromide (HBr);
  d) removing said dibromomethane from said third stream under separation conditions, to produce a dibromomethane stream and a fourth stream comprising unreacted methane, methyl bromide and hydrogen bromide;
  e) converting the fourth stream into chemicals;
  f) separating hydrogen bromide from said third stream and/or said fourth stream, to provide a hydrogen bromide-rich stream; wherein the step of separating hydrogen bromide is performed by non-aqueous extraction;
  g) subjecting the hydrogen bromide-rich stream of step (f) to an electrolysis step (g) to produce a hydrogen stream and/or a bromine stream, said bromine stream being optionally reused in step (c).

Surprisingly, this process allows the formation of activated methane under the form of methyl bromide, the activated methane comprising a low content of dibromomethane, for example, less than 5 mol % based on the total molar content of the sum of methyl bromide and dibromomethane; preferably less than 1 mol %; more preferably the activated methane is devoid of dibromomethane. This limits the formation of coke or carbonaceous components during further processing of methyl bromide. Therefore, the resulting process allows protecting one or more catalysts from coke contamination and subsequently an improved conversion of the methane into olefins, in particular into ethylene and/or propylene. The process also allows to recover the hydrogen bromide which is formed during the bromination reaction in order to produce hydrogen and/or bromine.

For example, the step (a) of providing a first stream comprising methane comprises providing a natural gas comprising methane at a content of at least 75 mol. % of the total molar content of said natural gas, preferably of at least 85 mol. %, more preferably of at least 90 mol. %, even more preferably of at least 95 mol. %.

For example, the step (a) of providing a first stream comprising methane comprises providing natural gas and purifying the natural gas to remove one or more selected from sulphur, nitrogen, oxygen, water and carbon dioxide.

For example, the bromine-rich stream comprises a mixture of hydrogen bromide and bromine; with a content of bromine being superior to 80 mol. % based on the total molar content of said stream; with preference, the content of bromine is at least 90 mol. % based on the total molar content of said stream, more preferably at least 95 mol. %, even more preferably at least 99 mol. %. Advantageously yet, the bromine-rich stream is a stream comprising only bromine.

For example, the bromination reaction conditions of step (c) include one or more of the following conditions:
  a molar ratio methane to bromine of at least 7:1, preferably of at least 5:1, more preferably of at least 3:1, even more preferably of at least 2.5:1;
  a pressure ranging from 0.1 MPa to 2.0 MPa, preferably ranging from 0.5 MPa to 1.5 MPa, more preferably ranging from 0.6 MPa to 1.0 MPa.

In the absence of catalyst, the bromination reaction conditions of step (c) include a temperature ranging from 350° C. to 550° C., preferentially from 390° C. to 500° C.

Alternatively, in the presence of one or more catalysts, the bromination reaction conditions of step (c) include a temperature ranging from 300° C. to 700° C. or from 400° C. to 700° C., preferentially from 350° C. to 450° C. or from 450° C. to 650° C.

For example, the separation conditions of step (d) comprise temperature conditions of at most 150° C., preferentially of at most 120° C.

For example, step (d) comprises a distillation column with temperature conditions of at most 150° C., preferentially of at most 120° C.

For example, the separation conditions of step (d) comprise pressure conditions ranging between 0.1 MPa and 2.0 MPa, preferentially between 0.1 MPa and 1.0 MPa or between 0.2 MPa and 1.0 MPa.

Optionally, the process of the present disclosure further comprises a step (f) of separating hydrogen bromide from said third stream and/or said fourth stream, so has to provide a hydrogen bromide-rich stream.

In a preferred embodiment, said electrolysis step (g) is carried out under gaseous phase or under liquid phase; with preference, said electrolysis is performed under water-free conditions.

For example, when the step (g) is performed under gaseous phase, said step (g) comprises temperature conditions ranging between 300° C. and 700° C., preferably between 350° C. and 650° C., more preferably between 400° C. and 600° C. For example, when the step (g) is performed under liquid phase, said step (g) comprises temperature conditions ranging between 20° C. and 80° C., preferably between 30° C. and 60° C., more preferably between 30° C. and 40° C.

For example, said step (g) is preferably performed under pressure conditions of at least 0.1 MPa, preferably ranging between 0.1 MPa and 2.0 MPa, more preferably ranging between 0.5 MPa and 1.5 MPa, even more preferably ranging from 0.6 MPa to 1.0 MPa.

For example, the dibromomethane stream of step (d) is further converted into carbon by performing carbonization of said dibromomethane stream, said carbonization is carried out using an electrical energy input and/or at a temperature of at least 500° C., or of at least 600° C., preferentially of at least 700° C., more preferentially of at least 1000° C., for example ranging between 500° C. and 3500° C., preferentially between 600° C. and 3000° C., more preferentially between 700° C. and 2500° C.

With preference, the conversion of the dibromomethane stream of step (d) into carbon is a process of conversion of dibromomethane into carbon black and/or graphite.

For example, the temperature which is required to produce carbon black is comprised between at least 500° C. and below 3000° C., preferably between 750° C. and 2000° C. When the temperature is above 2600° C., and up to 3500° C., production of graphite is favoured. Preferably, graphite is formed at a temperature comprised between 3000° C. and 3400° C.

For example, the step (e) of conversion of the fourth stream into chemicals comprises the following sub-steps:
i. providing a first catalytical composition comprising at least one homologation catalyst;
ii. putting into contact said fourth stream with the first catalytical composition under first reaction conditions to provide a first product stream comprising C1-C7 hydrocarbons and hydrogen bromide;
iii. optionally, providing a second catalytical composition comprising at least one cracking catalyst and putting into contact said first product stream with the second catalytical composition under second reaction conditions, to provide a second product stream comprising C1-C8 hydrocarbons and HBr;
iv. separating C2-C4 hydrocarbons from said first product stream and/or from said second product stream when sub-step (iii) is carried out, to form a C2-C4 stream;
with preference, said C2-C4 stream is further separated into an ethylene stream and/or into a propylene stream.

Said step (e) of conversion of the fourth stream into chemicals further comprises the sub-step (v) of separating an unreacted methane stream from said first product stream and/or from said second product stream when sub-step (iii) is carried out, to form a methane stream; with preference, said methane stream is recycled in the first stream of step (a) and/or said methane stream is purged to form a fuel gas stream.

For example, the first catalytical composition is steamed before sub-step (ii) and the one or more homologation catalysts of the first catalytical composition comprise one or more zeolites and a binder, wherein said one or more zeolites comprise at least one 10-membered ring channel.

For example, said one or more zeolites of the first catalytical composition contain less than 1000 wt. ppm of alkali metals based on the total weight of the one or more zeolites and/or less than 5000 wt. ppm of transition metals based on the total weight of the one or more zeolites. The content of the alkali metals is below 5000 wt. ppm based on the total weight of the one or more zeolites, preferably below 2500 wt. ppm. The content of the alkaline earth metals is below 5000 wt. ppm based on the total weight of the one or more zeolites, preferably below 2500 wt. ppm. However, the first catalytical composition may contain a higher content of alkaline earth metals as a component of the binder (e.g. $Ca_3(PO_4)_2$). So, additional traces of these metals may be present on the catalyst as impurities from the binder.

With preference, one or more of the following embodiments can be used to better define the first catalytical composition used in the present disclosure:
The first catalytical composition is blended with at least one metal-containing material; with preference, the at least one metal-containing material is an alkaline earth metal-containing material which comprises at least one alkaline earth metal is selected from beryllium, magnesium, calcium, strontium, barium and any mixtures thereof, and/or the at least one metal-containing material has an anion selected from the group of oxides, silicates, aluminates, titanates, phosphates, borates and borosilicates.

The first catalytical composition comprises between 0.1 wt. % and 7.0 wt. % of a phosphorus-containing material as based on the total weight of the first catalytical composition, preferably between 0.3 wt. % and 4.5 wt. %, preferentially between 0.5 wt. % and 4.0 wt. %, more preferentially 2.0 wt. %. In a preferred embodiment, the first catalytical composition is modified with 2.3 wt. % of phosphorous. Advantageously, the first catalytical composition modified with phosphorous is blended with at least one metal-containing material; with preference, the at least one metal-containing material is one or more selected from an alkaline earth metal-containing material; magnesium nitrate; and a cerium-containing material.

With preference, one or more of the following embodiments can be used to better define the one or more zeolites of the first catalytical composition used in the present disclosure:
The one or more zeolites of the first catalytical composition have a crystal size below 2000 nm, as determined by scanning electron microscopy (SEM), preferentially below 1750 nm, more preferentially below 1500 nm, even more preferentially below 1250 nm.
The one or more zeolites of the first catalytical composition have a Si/Al molar ratio of at least 10 before the step of steaming; and/or a Si/Al molar ratio of at least 80 after the step of steaming; with preference, of at least 150. With preference, the one or more zeolites of the first catalytical composition have a Si/Al molar ratio ranging from 80 to 1500 after the step of steaming; preferably ranging from 150 to 1200; more preferably ranging from 400 to 1100 and most preferably from 800 to 1000.
The one or more zeolites of the first catalytical composition are dealuminated with an organic acid solution or with an inorganic solution.
The one or more zeolites in the first catalytical composition are selected from the group of MFI, MEL, FER, MTT, MWW, TON, EUO and MRE families.
The one or more zeolites in the first catalytical composition are selected from the group of MFI, MEL, FER, MTT, MWW, TON, EUO and MRE families, and said one or more zeolites having a Si/Al molar ratio of at least 10 before the step of steaming; and/or a Si/Al molar ratio of at least 80 after the step of steaming; with preference, of at least 150. With preference, the one or more zeolites are selected from the MFI family, with a Si/Al molar ratio of at least 10.
The one or more zeolites of the first catalytical composition are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48.
The one or more zeolites of the first catalytical composition are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48, and said one or more zeolites having a Si/Al molar ratio of at least 10 before the step of steaming; and/or a Si/Al molar ratio of at least 80 after the step of steaming; with preference, of at least 150. With preference, the one or more zeolites of the first catalytical composition are ZSM-5, with a Si/Al molar ratio of at least 10.

The one or more zeolites have Brønsted acid sites in a concentration inferior to 100 µmol/g-cat as determined by $NH_3$-Temperature Programmed Desorption, preferentially inferior to 90 µmol/g-cat, more preferentially inferior to 80 µmol/g-cat.

With preference, one or more of the following embodiments can be used to better define the binder of the first catalytical composition used in the present disclosure:

The binder is selected from silica, clays, calcium phosphates, magnesium phosphates, and mullite. Most preferentially, the binder is silica.

The binder is devoid of aluminium compounds, such as alumina.

The binder is present in a content of at least 10 wt. % as based on the total weight of the first catalytical composition; preferably in a content of at least 20 wt. %, most preferably in a content of 30 wt. %, even more preferably in a content of at least 40 wt. %, and most preferably in a content of at least 50 wt. %.

In a preferred embodiment, the first catalytical composition is calcinated before said sub-step (ii); with preference, the first catalytical composition is calcined at a temperature of at least 400° C.

With preference, said steaming of the first catalytical composition before sub-step (ii) can be further defined with one or more of the following features:

Said steaming before sub-step (ii) is performed at a temperature ranging between 300° C. and 800° C., preferentially ranging between 400° C. and 750° C.

The one or more steamed zeolites of the first catalytical composition are leached with an organic or inorganic acid solution, before the sub-step (ii). The steaming and the leaching of the first catalytical composition are performed subsequently, the steaming step being conducted first.

Said step of steaming is carried out at a partial pressure of the steam ranging between 0.01 kPa and 20 kPa, preferentially between 0.5 kPa and 1.5 kPa.

Said step of steaming is followed by an extraction step, with preference with a monoprotic acid selected from HCl, $HNO_3$, HBr, acetic acid or formic acid.

Said step of steaming is followed by an extraction step, with preference with a complexing agent or with an aqueous complexing agent.

Said step of steaming is followed by an extraction step and by a calcination step; with preference, said calcination step is carried out in a steam-free atmosphere at a temperature ranging between 550° C. and 700° C., preferentially at a temperature ranging between 600° C. and 650° C.

Said step of steaming is followed by a calcination step; with preference, said calcination step is carried out in a steam-free atmosphere at a temperature ranging between 550° C. and 700° C., preferentially at a temperature ranging between 600° C. and 650° C.

Said step of steaming is followed by a step of modification of the steamed catalyst by phosphorous.

In an embodiment, said step of steaming of the first catalytical composition before sub-step (ii) is followed by a step of modification of the steamed catalyst by phosphorous under reduced or atmospheric pressure, preferentially at a temperature from 10 to 400° C., more preferably at a temperature from 50° C. to 350° C., even more preferentially at a temperature from 100° C. to 300° C. With preference:

The source of phosphorous in the modification step of the steamed catalyst is mixed in an aqueous or a non-aqueous medium.

The source of phosphorous in the modification step of the steamed catalyst is mixed in a non-aqueous medium selected from the group of ethanol, methanol and/or other alcohols.

The source of phosphorous is phosphoric acid, preferably a solution of phosphoric acid.

The modification step of the steamed catalyst is followed by a calcination step; with preference, said calcination step is carried out in a steam-free atmosphere at a temperature ranging between 550° C. and 700° C., preferentially at a temperature ranging between 600° C. and 650° C.

The modification step of the steamed catalyst is followed by a further step of steaming, preferentially at a steam partial pressure comprised between 0.1 and 1.0 kPa and/or at a temperature comprised between 550 and 750° C. and/or for a period of from 0.5 to 10 hours.

The modification step of the steamed catalyst is followed by a calcination step and by a further step of steaming, preferentially at a steam partial pressure comprised between 0.1 and 1.0 kPa and/or at a temperature comprised between 550 and 750° C. and/or for a period of from 0.5 to 10 hours.

For example, the first reaction conditions comprise
a temperature ranging between 250° C. and 460° C., preferably between 280° C. and 420° C., more preferably between 280° C. and 400° C.; and/or
a pressure ranging between 0.2 MPa and 1.5 MPa, preferably between 0.4 MPa and 1.0 MPa, more preferably between 0.5 MPa and 1.0 MPa; and/or
a weight hourly space velocity comprised between 0.1 $h^{-1}$ and 100 $h^{-1}$, preferably comprised between 1.5 $h^{-1}$ and 10 $h^{-1}$.

For example, wherein sub-step (iii) is carried out, said process is remarkable in that said at least one cracking catalyst comprises one or more zeolites and/or one or more clays. With preference, said at least one cracking catalyst comprises one or more zeolites selected from silicalites from the MFI family, crystalline silicate from the MFI family with a Si/Al atomic ratio of at least 180, crystalline silicate from the MEL family with a Si/Al atomic ratio ranging between 150 and 800, and/or phosphorous-modified zeolite from the MFI, MEL, FER, or MOR family.

For example, wherein sub-step (iii) is carried out, said at least one cracking catalyst comprises one or more zeolites selected from silicalites from the MFI family, optionally with a silica binder.

For example, wherein sub-step (iii) is carried out, said process is remarkable in that the second reaction conditions comprise
ranging from 400° C. to 600° C., preferably ranging from 425° C. to 575° C., more preferably ranging from 450° C. to 550° C.; even more preferably from 475° C. to 525° C.; and/or
a weight hourly space velocity comprised between 0.1 $h^{-1}$ and 100 $h^{-1}$, preferably comprised between 1.5 $h^{-1}$ and 10 $h^{-1}$; and/or
a pressure ranging between 0.2 MPa and 1.5 MPa, preferentially between 0.4 MPa and 1.0 MPa.

According to a second aspect, the present disclosure provides for an installation for carrying out the process of conversion of a stream comprising methane into chemicals according to the first aspect, said installation being remarkable in that it comprises:
- a bromination unit;
- a conversion unit;
- a physical separation unit;

wherein the bromination unit, the conversion unit and the physical separation unit are fluidically connected in series, the conversion unit being downstream of said bromination unit and upstream of said physical separation unit;

wherein said installation further comprises a first line to conduct the chemicals exiting the physical separation unit into one products-recovery unit;

wherein said installation further comprises a third line to conduct one hydrogen bromide-rich stream into an electrolysis unit.

With preference, said installation further comprises a second line to conduct the dibromomethane stream exiting the bromination unit to a carbonization reactor, preferably a fluidized bed reactor or a fixed bed reactor.

With preference, the carbonization reactor is a fluidized bed reactor.

For example, said conversion unit comprises one homologation reactor and optionally one cracking reactor.

For example.

For example, said bromination unit comprises at least one bromination reactor and at least one dibromomethane separator, the one or more dibromomethane separators being downstream of said at least one bromination reactor.

With preference, said installation further comprises a bromine-recovery unit, said bromine-recovery unit being downstream of said electrolysis unit and/or upstream of said bromination unit.

DETAILED DESCRIPTION

Figure 1:
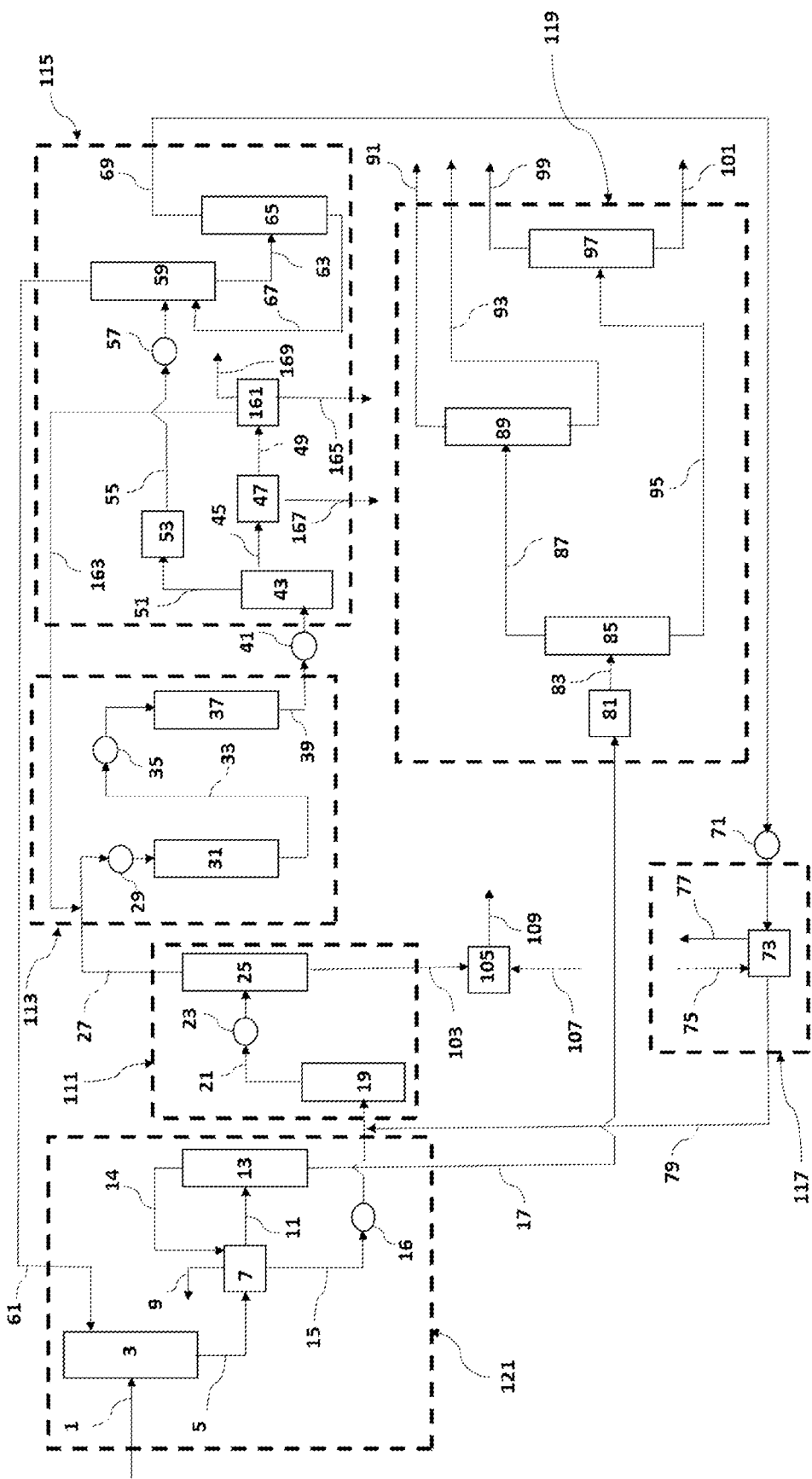
FIG. 1 illustrates the installation in accordance with the present disclosure, wherein the optional step (f) of the process is carried out in non-aqueous phase and wherein the electrolysis step (g) of the process is performed under gaseous phase.

For the disclosure, the following definitions are given:

The feed gas of the process, i.e. the first gaseous stream comprising methane, is preferably natural gas and/or other rich-methane hydrocarbon source assumed to be treated in outside battery limit (OSBL) plant where the majority of one or more selected from sulphur-containing compounds, water, carbon dioxide, oxygen and nitrogen are removed.

As used herein, the term "C #hydrocarbons", wherein "#" is a positive integer, is meant to describe all hydrocarbons having #carbon atoms. C #hydrocarbons are sometimes indicated as just C #. Moreover, the term "C #+ hydrocarbons" is meant to describe all hydrocarbon molecules having #or more carbon atoms. Accordingly, the expression "C2+ hydrocarbons" is meant to describe a mixture of hydrocarbons having 2 or more carbon atoms.

The symbol "=" in the term "C #=hydrocarbon" indicates that the hydrocarbon concerned is an olefin or an alkene, the notation "=" symbolizing the carbon-carbon double bond. For instance, "C6=" stands for "C6 olefin", or for "olefins comprising 6 carbon atoms".

LPG means "liquefied petroleum gas" and is a mixture of C3-C4 essentially composed by propane and butane.

Zeolite codes (e.g., MFI . . . ) are defined according to the "*Atlas of Zeolite Framework Types*", 6$^{th}$ revised edition, 2007, Elsevier, to which the present application also refers.

The Si/Al atomic ratio corresponds to the content of $SiO_2$ divided by the content of $Al_2O_3$ taking into account the fact there are two atoms of aluminium for one atom of silicon. The silicon to aluminium ratio (also stated as SAR) corresponds to the content of $SiO_2$ divided by the content of $Al_2O_3$ notwithstanding the proportion of the Si atoms over the Al atoms in the chemical formula of the zeolite. Therefore, the value of the SAR always corresponds to twice the value of the Si/Al atomic ratio.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics or embodiments may be combined in any suitable manner, as would be apparent to a person skilled in the art from this disclosure, in one or more embodiments.

The process and the installation for carrying out the process will be jointly described by reference to the figures. The text will describe the installation shown in FIGS. 1 to 3 at the same time, except when the features of the installation will differ between the three embodiments.

The disclosure provides a process and an installation for the conversion of natural gas into chemicals, in particular into ethylene, propylene, LPG, gasoline and hydrogen.

The process of the present disclosure is a process of conversion of a stream comprising methane into chemicals, said process being remarkable in that it comprises the following steps:
a) providing a first stream (1, 5, 15) comprising methane;
b) providing a second stream 79, which is a bromine-rich stream;
c) putting into contact said first stream 15 with said second stream 79 under bromination reaction conditions to obtain a third stream 21 comprising at least unreacted methane, methyl bromide, dibromomethane, and hydrogen bromide;

d) removing said dibromomethane from said third stream 21 under separation conditions, to produce a dibromomethane stream 103 and a fourth stream 27 comprising unreacted methane, methyl bromide and hydrogen bromide;

e) converting the fourth stream 27 into chemicals;

f) separating hydrogen bromide from said third stream 21 and/or said fourth stream 27, to provide a hydrogen bromide-rich stream 69, wherein the step of separating hydrogen bromide is performed by non-aqueous extraction;

g) subjecting the hydrogen bromide-rich stream 69 of step (f) to an electrolysis step (g) to produce a hydrogen stream 77 and/or a bromine stream 79, said bromine stream 79 being optionally reused in step (c).

The first stream (1, 5, 15) is the feed stream of the process. According to the disclosure, the first stream (1, 5, 15) is or comprises natural gas. For example, the first stream (1, 5, 11) is a natural gas comprising methane. For example, the first stream (1, 5, 11) is a natural gas comprising methane at a content of at least 75 mol. % of the total molar content of said natural gas; preferably at least 85 mol. %, more preferably at least 90 mol. %, and even more preferably of at least 95 mol. % of methane.

The first stream (1, 5, 15) comprises methane, and also C2+ hydrocarbons. The C2+ hydrocarbons present in the first stream (1, 5, 15) may include, for example, lower molecular weight alkanes. As used herein, the term "lower molecular weight alkanes" refers to methane, ethane, propane, butane, pentane, or mixtures thereof.

Pre-Treatment of Natural Gas

To start the process, the first stream 1 is advantageously injected into a pre-treatment unit 121 of natural gas. The pre-treatment unit 121 can comprise a demethanizer 13 to separate the methane from the first stream (1, 5). At least a part 11 of the first stream (1,5) is directed to the demethanizer. A methane stream (14, 15) and a C2-C4 hydrocarbons stream (17, 83) are thus separated. For example, the pre-treatment unit 121 may also include a purification unit 3. In this case, the first stream 1 comprising methane can be subjected to an optional preliminary step of purification to remove one or more selected from sulphur, nitrogen, water and carbon dioxide. Said purification unit 3 is placed upstream to the demethanizer 13. The pre-treatment unit 121 of natural gas may also comprise one or more heat exchangers, such as one or more cold boxes 7 disposed on a line upstream of the demethanizer 13. The purified first stream 5 exiting from the purification unit 3, or the first stream 1 comprising methane, can be conveyed into the cold box 7, to provide a first stream 11 having its temperature adapted to the operating conditions of the demethanizer 13. For example, the demethanizer 13 is a cryogenic distillation column. For example, the operating conditions of the demethanizer 13 comprise a temperature ranging between −120° C. and −80° C., preferably between −110° C. and −90° C., and/or a pressure ranging between 2.5 MPa and 3.5 MPa. After its passage within the demethanizer 13, a stream 14 of methane having a temperature inferior to the first stream (1, 5) is redirected to the cold box 7 for cooling the first stream (1, 5).

The stream (1, 5, 14) comprising methane can be purged, to recover a fuel gas stream 9.

The methane stream 15 exiting the cold box 7 can be conveyed into an additional heat exchanger 16 before exiting the pre-treatment unit 121.

The C2-C4 hydrocarbons stream (17, 83) separated from the first stream (1, 5, 11) can be conveyed into one products-recovery unit 119 of the installation (see below).

Activation of the Methane

Figure 2:
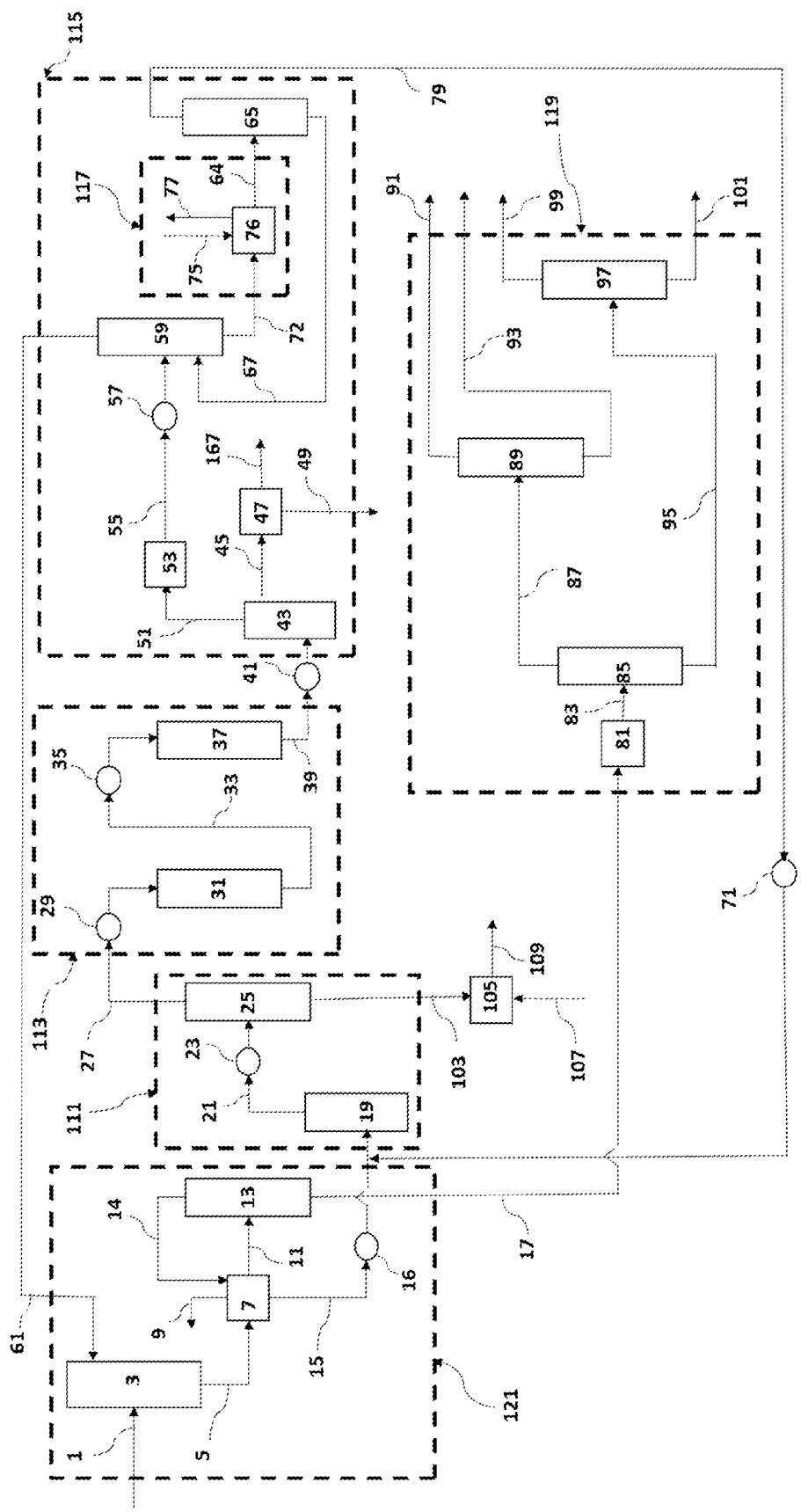
FIG. 2 illustrates the installation in accordance with the present disclosure, wherein the optional step (f) of the process is carried out in non-aqueous phase and wherein the electrolysis step (g) of the process is performed under liquid phase.
Figure 3:
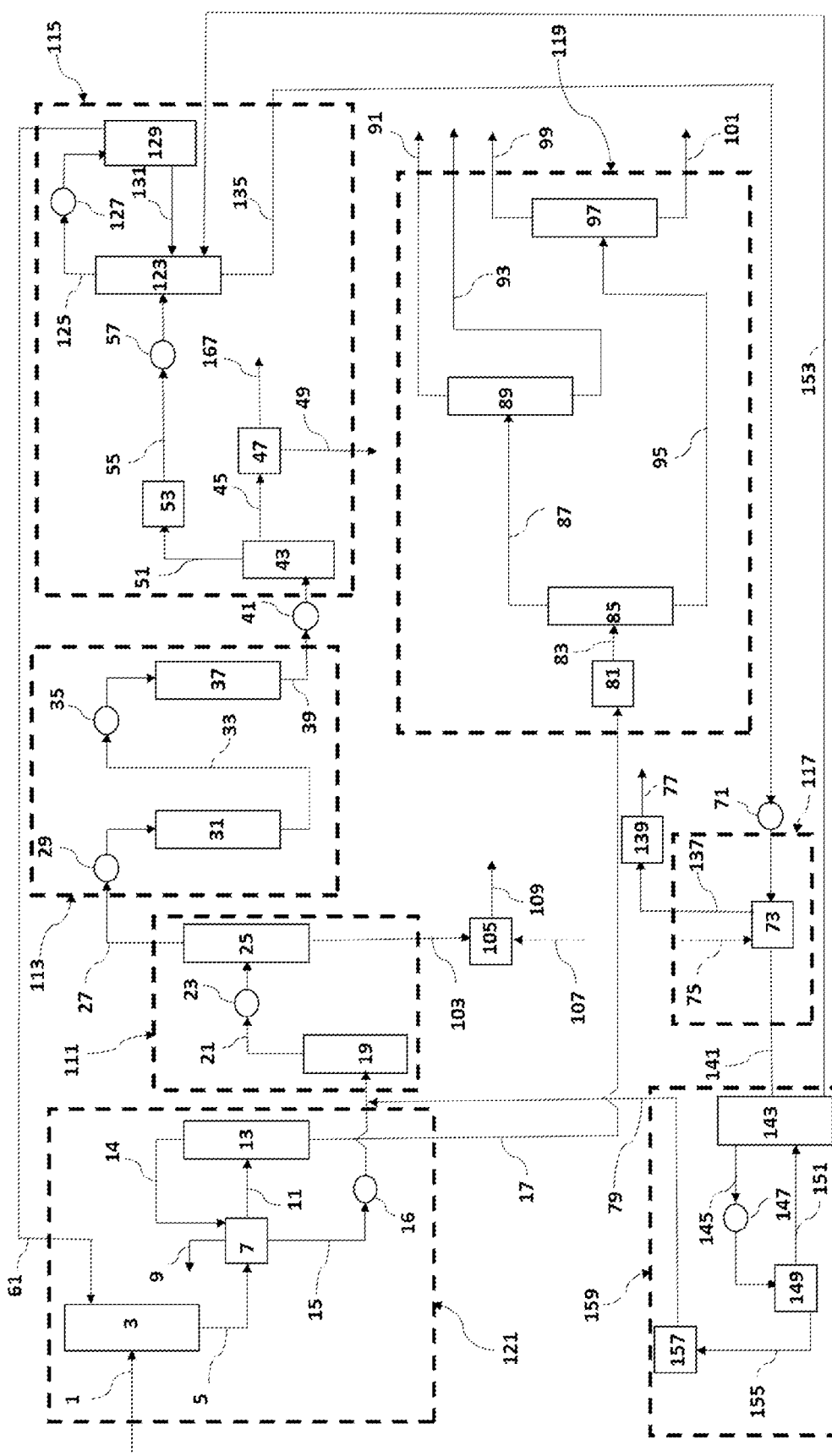
FIG. 3 illustrates an installation wherein the optional step (f) of the process is carried out in aqueous phase and wherein the electrolysis step (g) of the process is performed under aqueous phase.

Upon its exit from the pre-treatment unit 121, the methane stream 15 can be put into contact with a second stream 79 which is a bromine-rich stream and then introduced into a bromination reactor 19 of one bromination unit 111 as shown on any of the FIGS. 1 to 3. Alternatively, the second stream 79 comprising bromine can be put in contact with the methane stream 15 within the bromination reactor 19 (not shown).

The second stream is a bromine-rich stream which can be a stream comprising a mixture of hydrogen bromide and bromine with a content of bromine being superior to 50 mol. % based on the total molar content of said stream. With preference, the content of bromine is at least 80 mol. %, more preferably at least 90 mol. %, even more preferably at least 95 mol. %. The activation of methane works better when the bromine-rich stream is devoid of hydrogen bromide or any other contaminants and comprises only bromine.

To have high selectivity in methyl bromide, it is advantageous to operate the bromination of methane stream 15 with an excess of methane, for example, the molar ratio methane to bromine can be advantageously high, for example, the molar ratio methane to bromine can be of at least 7:1, preferably at least 5:1, more preferably at least 3:1, even more preferably at least 2.5:1. For instance, the molar ratio methane to bromine is ranging from 2.5:1 to 12:1, preferably of about 3:1 to about 10:1. Under these conditions, the reaction selectivity may be above 80% for methyl bromide and less than 20% dibromomethane, on a molar basis.

The bromination reaction conditions of step (c) include a pressure of at least 0.1 MPa; preferably, ranging from 0.1 MPa to 2.0 MPa; more preferably ranging from 0.5 to 1.5 MPa, and more preferably ranging from 0.6 to 1.0 MPa.

In a first alternative, and in a preferred example, step (c) can be performed in the absence of a catalyst. The bromination reaction conditions of step (c) when no catalysts are involved include a temperature ranging from 300° C. to 550° C. or from 350° C. and 550° C., or from 300° C. to 500° C., or from 390° C. and 500° C.

In a second alternative, step (c) can be performed in the presence of a catalyst. The bromination reaction conditions of step (c) when at least one catalyst is involved include a temperature ranging between 300° C. and 700° C. or 400° C. and 700° C., preferably between 350° C. and 450° C. or between 450° C. and 650° C.; more preferably between, 500° C. and 600° C. Thus, either solid strongly acidic catalysts or (supported Group VIII metal (particularly platinum and palladium) catalysts are capable of catalyzing the gas-phase bromination of methane predominantly to methyl bromide in 85 to 99% selectivity, Subsequent or concurrent catalytic hydrolysis can produce methyl alcohol and/or dimethyl ether.

A particularly useful class of solid, strongly acidic catalysts are those derived from halides, oxyhalides, oxides, sulfides and oxysulfides of metals, particularly transition metals of Groups IV, V, VI, VIII of the Periodic Table, such as of tantalum, niobium, zirconium, tungsten, titanium, chromium, and the like, or mixtures thereof, deposited on suitable chalconite carriers, such as alumina, zirconia or silica-alumina. These catalysts are capable of effecting the ready conversion of methane to methyl halides.

As noted in Olah, G. A. "Friedel-Crafts Chemistry," N.Y., Wiley-Interscience, 1973, p. 343-344, the elements of Group VIA such as oxygen, sulfur, selenium or tellurium, have been called "chalcogens", and compounds containing these elements are called "chalconites", "chalcogenides" or "chalcides". A variety of solid oxides and sulfides, especially those comprising alumina, silica and mixtures of alumina and silica, either natural or synthetic, in which other oxides such as chromia, magnesia, molybdena, thoria, tungstic oxide, zirconia, etc., may also be present, as well as sulfides of molybdenum are useful chalcide carriers. Many naturally occurring compositions exist for use as the carriers including bauxite, floridin, Georgia clay, and other natural aluminosilicates.

Synthetic chalconites other than those of the silica-alumina type, representative of the chalconite carriers are: BeO, $Cr_2O_3$, $P_2O_5$, $ThO_2$, $TiO_2$, $Al_2(SO_4)_3$ (which may be regarded as $Al_2O_3 \cdot 3SO_3$), $Al_2O_3 \cdot Cr_2O_3$, $Al_2O_3$, $Fe_2O_3$, $Al_2O_3 \cdot CoO$, $Al_2O_3 \cdot MnO$, $Al_2O_3 \cdot V_2O_3$, $Al_2O_3 \cdot Mo_2O_3$, $Cr_2O_3 \cdot Fe_2O_3$, $MoS_2$, and $MoS_3$.

The acidic chalconite supports are physically and chemically stable. They are generally catalytically active at only higher temperatures, as their acidity is not great enough to lead them to form stable complexes with unsaturated compounds, as do the aluminium halides, for example.

The supported Group VIII metal catalysts include the various Group VIII metals supported on suitable chalconite carriers. Particularly useful platinum and palladium supported on alumina, silica, barium sulfate or related carriers.

Separation of Dibromomethane

At the exit of the bromination reactor 19, a third stream 21 comprising at least methyl bromide, dibromomethane and hydrogen bromide is then conveyed into a dibromomethane separator 25. For example, the dibromomethane separator 25 can be one or more distillation columns and/or one or more adsorption columns and/or one or more absorption columns, preferably one or more distillation columns. The third stream 21 can be advantageously directed into a heat exchanger 23 to adjust its temperature before entering into the dibromomethane separator 25.

For example, the separation conditions that are operated during the step (d) are based on the boiling point (measured under atmospheric pressure, i.e. about 0.1 MPa) of the dibromomethane (96.95° C.), of the methyl bromide (3.56° C.), methane (−161.5° C.) and hydrogen bromide (−66° C.). Therefore, when distillation is carried out in one or more distillation columns, it is relatively simple to collect the volatile fraction made of compounds having low boiling points by performing the distillation under temperature conditions of at most 50° C., preferentially of at most 120° C. The pressure conditions operated during step (d) are therefore comprised between 0.1 MPa and 1.0 MPa.

A dibromomethane stream 103, which is a non-volatile stream, is then removed from said third stream 21.

By placing a fluidized bed reactor, preferably an electrothermal fluidized bed reactor 105, at one output line of the dibromomethane separator 25, it is possible to subject the dibromomethane stream 103 to a carbonization step to produce carbon 109. The carbonization step is carried out using an electrical energy input 107 and/or at a temperature of at least 500° C., or of at least 600° C., preferably of at least 800° C., more preferably of at least 1000° C. For example, the carbonization step is carried out at a temperature ranging between 500° C. and 3500° C., preferably between 600° C. and 3000° C. Graphite can advantageously be obtained when the temperature is ranging between 2600° C. and 3500° C., preferably between 3000° C. and 3400° C.

Carbon black can advantageously be obtained when the temperature is ranging between 500° C. and below 3000° C. For example, the fluidized bed reactor can be fluidized thanks to an inert gas flux, such as a flux of nitrogen, argon and/or helium.

The volatile stream exiting the dibromomethane separator 25 is recovered in a fourth stream 27 comprising at least unreacted methane, methyl bromide and hydrogen bromide.

Conversion into Chemicals

The fourth stream 27 is conveyed to a conversion unit 113, comprising at least one homologation reactor 31 and optionally, at least one cracking reactor 37.

The fourth stream 27 is then enriched into C2-C4 hydrocarbons to generate valuable chemicals that can be recovered into a C2-C4 stream (17, 83) and further separated into interesting compounds, such as ethylene and/or propylene, but also liquefied petroleum gas.

The step (e) of conversion of the fourth stream 27 into chemicals comprises the following sub-steps:
 i. providing a first catalytical composition comprising at least one homologation catalyst,
 ii. putting into contact said fourth stream 27 with the first catalytical composition under first reaction conditions to provide a first product stream 33 comprising C1-C7 hydrocarbons and hydrogen bromide;
 iii. optionally, providing a second catalytical composition comprising at least one cracking catalyst and putting into contact said first product stream 33 with the second catalytical composition under second reaction conditions, to provide a second product stream 39 comprising C1-C8 hydrocarbons and HBr;
 iv. separating C2-C4 hydrocarbons from said first product stream 33 and/or from said second product stream 39 when sub-step (iii) is carried out, to form a C2-C4 stream (17, 83).

Sub-Step (i): Providing the First Catalytical Composition

For performing this enrichment, a homologation reactor 31 loaded with a first catalytical composition comprising one or more homologation catalysts is placed downstream of the dibromomethane separator 25. For example, the homologation reactor 31 can be selected from a fixed bed reactor or a fluidized bed reactor, preferably a fixed bed reactor. The installation may comprise one or more heat exchangers 29 arranged between the dibromomethane separator 25 and the homologation reactor 31 so that one or more steps of adjusting the temperature of the fourth stream 27 before it enters the homologation reactor 31 is included.

The first catalytical composition comprising one or more zeolites and a binder is steamed before used in sub-step (ii) and said one or more zeolites comprise at least one 10-membered ring channel.

It is preferred that the one or more zeolites, namely the one or more zeolites before the step of steaming, or the non-steamed one or more zeolites, do not contain any alkali metals since these metals may significantly reduce catalyst activity and neutralize acid sites. In a preferred embodiment, said one or more zeolites initially contain less than 1000 wt. ppm of alkali metals, as based on the total weight of the one or more zeolites.

It is preferred that the one or more zeolites, namely the one or more zeolites before the step of steaming, do not contain any alkaline earth metal since these metals may impact the steam dealumination process and retain halogen after the reaction. The retained halogen will be released during the regeneration and irreversibly deactivate zeolites.

In the case where the one or more zeolites are doped with at least one phosphorus-containing material and at least one alkaline earth metal-containing material, the alkaline earth metal is strongly bound with the phosphorous and is less prone to the formation of halides.

In a preferred embodiment, said one or more zeolites, before the steaming step, contain less than 5000 wt. ppm of alkaline earth metals, as based on the total weight of the one or more zeolites.

It is preferred that the first catalytical composition does not contain any transition metal since this leads to a completely distinct reactivity resulting in coke formation. This is why the first catalytical composition is devoid of any transition metal. This means that the content of the transition metals is below 5000 wt. ppm in the one or more zeolites, preferably below 2500 wt. ppm in the one or more zeolites. Traces of these metals may be present on the catalyst as impurities from the binder.

The one or more zeolites comprise at least one acid 10-membered ring channel; with preference, the one or more zeolites are selected from the list comprising MFI, MEL, FER, MTT, MWW, TON, EUO and MRE families, preferentially from the MFI family or the MEL family. These zeolites or molecular sieves are aluminosilicate catalysts that have a chemical structure that is largely different from the chemical structure of the aluminophosphate and silicoaluminophosphate molecular sieves.

With preference, the zeolite from the MFI family is selected from ZSM-5, silicalites, boralite C, or TS-1. Preferentially, the zeolites are silicalites from the MFI family or ZSM-5, more preferentially the zeolites are silicalites from the MFI family. The zeolites from the MEL family are, preferentially, selected from ZSM-11, silicalites, boralite D, TS-2, or SSZ-46. Preferentially, the zeolites are silicalites from the MEL family. The zeolites from the FER family are, preferentially, selected from ferrierite, FU-9 or ZSM-35. The zeolites from the MTT family are, preferentially, ZSM-23. The zeolites from the MWW family are, preferentially, selected from MCM-22, PSH-3, ITQ-1, or MCM-49. The zeolites from the TON family are, preferentially, selected from ZSM-22, Theta-1, or NU-10. The zeolites from the EUO family are, preferentially, selected from ZSM-50 or EU-1. The zeolites from the MRE family are, preferentially, ZSM-48.

Therefore, in a preferred embodiment, the first catalytical composition comprises one or more zeolites with at least one acid 10-membered ring channel.

Advantageously, the one or more zeolites have a crystal size below 2000 nm as determined by scanning electron microscopy (SEM), preferentially below 1750 nm, more preferentially below 1500 nm and even more preferentially below 1250 nm. The fact that one or more zeolites have a small size allows for better accessibility of the reactants to the catalyst, which renders the catalyst more active.

The first catalytical composition comprising one or more zeolites is steamed before the step (c) of contacting said feedstream with the said first catalytical composition under reaction conditions to obtain a higher Si/Al molar ratio relative to the non-steamed one or more zeolites.

Advantageously, the one or more zeolites are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48, said one or more zeolites having a Si/Al molar ratio of at least 10 before the step of steaming.

Advantageously, the one or more zeolites are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48, said one or more zeolites having a Si/Al molar ratio of at least 80 after the step of steaming; with preference, of at least 150.

In a preferred embodiment, the first catalytical composition comprises 3D zeolites without cages (cavities) and containing at least one acid 10-membered ring channel.

Preferably, the first catalytical composition comprises at least 60 wt. % of one or more zeolites having at least one acid 10-membered ring channel, more preferably at least 70 wt. %, even more preferably at least 80 wt. % and most preferably at least 90 wt. % or 95 wt. %, or 100 wt. %.

To provide an appropriate acidity, it is preferred that the one or more zeolites are at least partly in their hydrogen form or at least partly in their ammonia form. Preferably more than 50 wt. % of the total content of the zeolites used are in their hydrogen form or their ammonia form, preferably at least 80 wt. %, more preferably at least 90 wt. %, and even more preferably 100 wt. % of the zeolites are in their hydrogen form or their ammonia form.

The one or more zeolites have weak Brønsted acid sites in a concentration inferior to 40 μmol/g-cat and strong Brønsted acid sites in a concentration superior to 40 μmol/g-cat as determined by $NH_3$-TPD. The one or more zeolites have Brønsted acid sites in a concentration inferior to 100 μmol/g-cat as determined by $NH_3$-TPD, preferentially inferior to 90 μmol/g-cat, more preferentially inferior to 80 μmol/g-cat. This can be obtained by performing a step of steaming the one or more zeolites before the contact of the first catalytical composition with the fourth stream 27.

Figure 4:
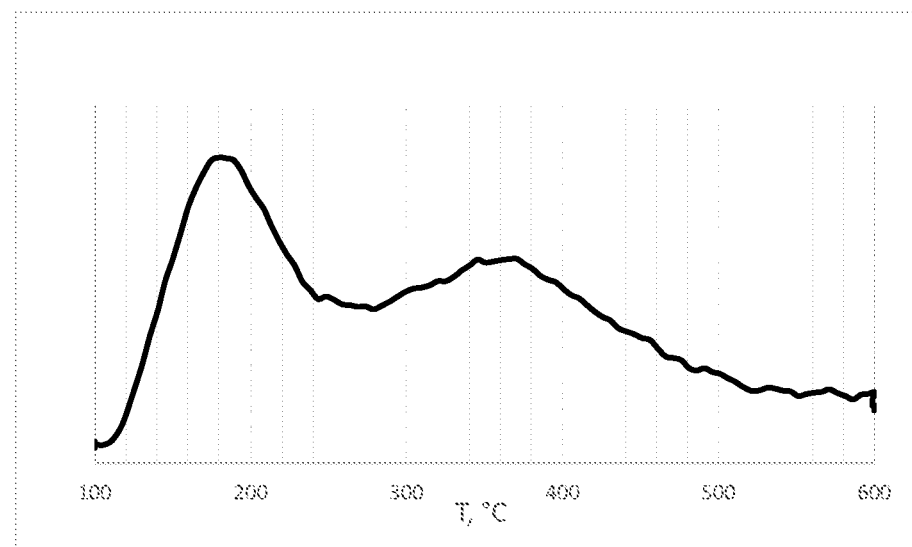
FIG. 4 shows the $NH_3$-TPD profile of the catalyst of the first catalytical composition according to the present disclosure.

The acidity of the zeolite catalyst was measured by $NH_3$-TPD. Generally, a temperature at which $NH_3$ is desorbed is an estimation of the strength of an acid site, i.e. higher the desorption temperature stronger is the acid site. The zeolite catalyst shows two $NH_3$-TPD peaks, a first one at 184° C. and a second at 363° C. (FIG. 4).

The one or more zeolites used in the first catalytical composition of the disclosure have a Si/Al molar ratio of at least 10 before the step of steaming, The Si/Al molar ratio before the step of steaming is typically ranging from 10 to 1500; preferably ranging from 80 to 1200; more preferably ranging from 150 to 1100 and most preferably from 800 to 1000.

The formation of extra-framework Al species is known to affect the pore structure and the porosity of the zeolite. Therefore, the removal of a large fraction of Al from the lattice leads to rearrangements of Si-T (tetrahedron) atoms and hence to the generation of large voids in the structure. The presence of such pores is crucial to obtain a high catalytic activity. Moreover, less aluminium also contributes to low coke formation and low ageing rates.

The steam treatment is conducted at elevated temperature, preferably in the range of from 300 to 800° C., more preferably in the range of from 400 to 750° C. and at a partial pressure of steam from 0.01 to 20 kPa, preferentially from 0.5 to 1.5 kPa. Preferably, the steam treatment is conducted at partial pressure of steam at least 1.5 kPa in the temperature range 300-450° C. If the temperature is above 450° C., the steam treatment is conducted in an atmosphere comprising the steam partial pressure below 1.5 kPa. The concentration of steam in the flow is between 1 to 100%, more preferably from 5 to 20% of steam. The diluent is a gas selected from the group of $N_2$, air, natural gas, $CO_2$ or a mixture of thereof. The steam treatment is preferably carried out for a period of from 0.1 to 200 hours, more preferably from 0.2 hours to 24 hours. As stated above, the steam treatment tends to reduce the content of tetrahedral aluminium in the crystalline silicate framework, by forming alumina. The particular effect consists in reducing the strong Brønsted external acidity of the zeolites.

One or more zeolites used in the first catalytical composition of the disclosure have a Si/Al molar ratio of at least 80 after the step of steaming, The Si/Al molar ratio after the step of steaming is typically ranging from 80 to 1500; preferably ranging from 150 to 1200; more preferably ranging from 400 to 1100 and most preferably from 800 to 1000.

Optionally, following the steam treatment, an extraction step is performed to remove the partially dislodged alumina species by leaching. The leaching is performed by a monoprotic acid selected from the HCl, $HNO_3$, HBr, acetic or formic or with a complexing agent which tends to form a soluble complex with alumina. The complexing agent is preferably in an aqueous solution thereof. The complexing agent may comprise an organic acid such as citric acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. A particularly preferred complexing agent may comprise an amine, preferably ethylene diamine tetraacetic acid (EDTA) or a salt thereof, in particular, the sodium salt thereof.

Following the step of steaming, the catalyst is advantageously thereafter calcined in absence of steam (<1% of steam) at a temperature of from 550 to 700° C. at atmospheric pressure for a period of from 0.5 to 10 hours.

Advantageously, the one or more zeolites comprise at least one 10-membered ring channel, with crystal size below 2000 nm, and have a Si/Al molar ratio ranging from 10 to 1500 after the step of steaming; preferably ranging from 80 to 1200; more preferably ranging from 150 to 1100 and most preferably from 800 to 1000. The one or more zeolites are preferably zeolites selected from the silicalites from the MFI family and/or silicalites from the MEL family having a Si/Al molar ratio of at least 10 before the step of steaming; and/or a Si/Al molar ratio of at least 80 after the step of steaming; with preference, of at least 150. In a more preferred example, the zeolite is ZSM-5.

Optional Modification of the Steamed First Catalytical Composition with Phosphorus Optionally, following the steaming step of the first catalytical composition, said steamed first catalytical composition is further modified by phosphorous under reduced or atmospheric pressure at a temperature from 10 to 400° C. A non-limiting source of phosphorus can be provided in an aqueous or non-aqueous medium.

In an embodiment, the non-limiting source of phosphorus is dissolved in a non-aqueous medium selected from the group containing ethanol, methanol or other alcohols.

The doping with a phosphorus-containing material consists of a steaming step followed by a leaching step using a solution of phosphoric acid ($H_3PO_4$) or using any acid solution containing the source of phosphorus. It is generally known by the persons in the art that steam treatment of zeolites results in aluminium that leaves the zeolite framework and resides as aluminiumoxides in and outside the pores of the zeolite. This transformation is known as the dealumination of zeolites. The treatment of the steamed zeolite with an acid solution results in the dissolution of the extra-framework aluminiumoxides. This transformation is known as leaching. Then the zeolite is separated, advantageously by filtration, and optionally washed. A drying step can be envisaged between the filtering and washing steps. The solution after the washing can be either separated, by way of example, by filtering from the solid or evaporated. The residual phosphorus-content is adjusted by the phosphorus concentration in the leaching solution, drying conditions, and washing procedure if any. This procedure leads to dealumination of zeolites and retention of phosphorus. Advantageously, at least 0.1 wt. % and up to 7.0 wt. % of phosphorus is retained after dealumination on zeolite. For example, the first catalytical composition advantageously comprises at least 0.1 wt. % of phosphorous based on the total weight of the first catalytical composition, preferentially with at least 0.5 wt. % of phosphorous, more preferentially with at least 1.0 wt. % of phosphorous, even more preferentially with at least 1.5 wt. % of phosphorous. Both factors dealumination and the retention of phosphorus stabilize the lattice aluminium in the zeolitic lattice, thus avoiding further dealumination. This leads to higher hydrothermal stability, tuning of molecular sieves properties and adjustment of acid properties. The degree of dealumination can be adjusted by the steaming and leaching conditions.

The preferred techniques suitable for the modification by phosphorous are impregnation and chemical vapour deposition.

These techniques imply a minimum waste to treat and allow maintaining substantially all phosphorus on the catalyst.

In an embodiment, the phosphorus is introduced by a treatment of the catalyst in a solution containing a source of phosphorus at a temperature ranging between 25 and 100° C. for 0.1-96 h followed by filtering or evaporation.

In a preferred embodiment, the incipient wetness (IW) impregnation techniques are used. In these IW impregnation techniques, the phosphorus is introduced via impregnation using a limited amount of liquid water which is subjected to contact with the catalyst. This method is also known as dry impregnation.

Incipient wetness (IW) or incipient wetness impregnation (IWI) is a commonly used technique for the synthesis of heterogeneous catalysts. Typically, the precursor (phosphorus-containing compounds) is dissolved in an aqueous or organic solution. The volume of solution, which is used for dissolution of the precursor, is substantially the same as the pore volume of catalyst precursor containing both binder and zeolite. Then the precursor-containing solution is added to a catalyst precursor. Capillary action draws the solution into the pores. The catalyst can then be dried and calcined to drive off the volatile components within the solution, depositing the phosphorus on the catalyst surface.

The sample before impregnation can be dried or calcined. The impregnation could be performed at room or elevated temperature.

The adsorption capacity is typically measured by impregnating the dried extruded zeolite with water until the zeolite was completely wet. Weighing the zeolite before and after impregnation gives the absorption capacity according to formula (1):

$$\text{Absorption capacity (\%)} = \frac{\text{weight after impregnation} - \text{dry weight}}{\text{dry weight}} * 100 \quad (1)$$

In an embodiment, $H_3PO_4$ solution is used for impregnation.

Advantageously, a mixture of $H_3PO_4$ with their ammonium salts providing a pH of the aqueous solution higher than 2.0 is used for impregnation.

In an embodiment, the sources of phosphorus are substantially metal-free components, for example, $H_3PO_4$, ammonium phosphates or organic phosphorous-compounds. By way of example, this proportion can be below 1000 wt. ppm of the total weight of the phosphorous-containing material.

The content of phosphorus in the catalyst can be from 0.1 to 30.0 wt. %, preferably from 0.3 to 9.0 wt. %. The content of phosphorous on the catalyst is most preferably 2.0 wt. %.

Following the introduction of phosphorous, the catalyst is thereafter calcined and/or steamed at a steam partial pressure between 0.1 and 1 kPa at a temperature of from 550 to 750° C. at for a period of from 0.5 to 10 hours.

Steaming, in addition to trigger aluminium leaching also allows for the reduction of the number of acid sites.

The crystalline alumino-silicate oxide framework of the one or more zeolite has a portion of the aluminium that is substituted with boron and/or titanium. Preferentially, boron is used to substitute one or more aluminium atoms in the zeolite framework. Boron-substituted zeolite has a very weak acidity. The zeolite catalysts have a Si/(Al+B) molar ratio of at least 80, typically comprised between 100 and 1200, preferentially of 1000.

Optional Modification of the Phosphorous Modified Steamed Catalyst

The first catalytical composition modified with a phosphorous containing-material may contain a metal-containing material, which is preferably an alkaline earth metal-containing material. However, the alkaline earth metal-containing material is spatially separated from the zeolite, in which alkaline earth metal is strongly bounded with phosphorous. The said alkaline earth metal is selected from the group of beryllium, magnesium, calcium, strontium, barium and any mixtures thereof.

The metal-containing material that can be added to a catalytical composition modified with phosphorous is advantageously in the form of alkaline earth metal salts and comprise at least one inorganic anion selected preferably from the group of oxides, silicates, aluminates, titanates, phosphates, borates and borosilicates. Suitable silicate anions include $SiO_3^{2-}$, $SiO_4^{4-}$, $Si_2O_7^{6-}$ and so on. Suitable borate anions include $BO_2^-$, $BO_3^{2-}$, $B_2O_5^{4-}$, $B_4O_7^{2-}$, $B_6O_{11}^{4-}$, $B_{10}O_{19}^{8-}$ and so on. Suitable aluminate anions include $Al_2O_4^{2-}$, $AlO_4^{5-}$, $Al_6O_{18}^{18-}$ and so on. Suitable titanate anions include $TiO_3^{2-}$, $Ti_3O_7^{2-}$, $Ti_4O_9^{2-}$, $TiO_4^{4-}$ and so on. Suitable phosphate anions include $PO_4^{3-}$, $HPO_4^{2-}$, $H_2PO_4^-$, $P_nO_{3n+1}^{(n+2)-}$ and so on. Bi-, tri- and poly-metal silicates, borates and borosilicates containing one, two or more alkaline earth metals selected from the list above can be used too. The metal salt may also comprise other anions.

Examples of suitable alkaline earth metal salts that can be added to a catalytical composition modified with phosphorous include $Mg_6Al_2CO_3(OH)_{16} \cdot 4(H_2O)$ (hydrotalcite), $Mg_2B_2O_5 \cdot H_2O$, $CaMgB_6O_{11} \cdot 6H_2O$ (hydroboracite), $Ca_2B_6O_{11} \cdot 5H_2O$ (colemanite), $Ca_4B_{10}O_{19} \cdot 7H_2O$, $Mg(BO_2) \cdot 8H_2O$, $Ca(BO_2) \cdot 2H_2O$, $BaB_6O_{10} \cdot 4H_2O$, $CaSi_6O_{17}(OH)_2$ (xonotlite), $CaMg(Si_2O_6)_x$, $Mg_2(Si_2O_6)_x$, $CaAl_2Si_2O_8$, $Mg_4Si_6O_{15}(OH)_2 \cdot 6H_2O$ (sepiolite), $(Mg,Al)_2Si_4O_{10}(OH) \cdot 4H_2O$ (palygorskite or attapulgite) and mixtures thereof.

A further example of suitable alkaline earth metals that can be added to a catalytical composition modified with phosphorous is $Mg(NO_3)_2$ (magnesium nitrate).

Before mixing with the molecular sieve, said alkaline earth metal salts may be modified by calcination, steaming, ion-exchange, impregnation, and/or phosphatation. Said alkaline earth metal salts may be an individual compound or may be a part of mixed compounds, for example, mixed with mineral, natural or chemical fertilizer.

The first catalytical composition of the present disclosure modified with at least one phosphorous-containing material and at least one alkaline earth metal-containing material has for effect to increase the selectivity to olefins (i.e. acyclic C3-C6 olefins) and to decrease subsequently the rate of the alkane formation (i.e. C3-C6 alkanes).

In a preferred embodiment, the first catalytical composition modified with phosphorous further comprises from 1 to 50 wt. % of hydrotalcite as based on the total weight of the first catalytical composition; with preference from 5 to 25 wt. %. The hydrotalcite is of the formula $Mg_6Al_2CO_3(OH)_{16} \cdot 4(H_2O)$.

In another preferred embodiment, the one or more zeolites are doped with both at least one phosphorus-containing material and with at least one alkaline earth metal-containing material, preferably at least one magnesium-containing material and/or at least one calcium-containing material.

The Shaping of the Catalyst with a Binder

According to the disclosure, one or more zeolites are shaped with a binder, which is an inorganic material, and preferentially silica. The zeolites shaped with the binder forms a catalytical composition, and the catalytical composition of the present disclosure preferably comprises at least 10 wt. % of a binder, at most 40 wt. % as based on the total weight of the first catalytical composition and at most 40 wt. %. Typically, the first catalytical composition of the present disclosure comprises between 20 wt. % and 25 wt. % of a binder as based on the total weight of the first catalytical composition.

The preferred binder is selected from silica, alpha-alumina, clays, alumina phosphates, calcium phosphates, magnesium phosphates, and mullite. Most preferentially, the binder is silica.

The binder preferably does not contain any aluminium compounds, such as alumina. This is because as mentioned above the preferred catalyst for use in the disclosure is de-aluminated by steaming to increase the Si/Al molar ratio of the crystalline silicate. The presence of alumina in the binder, as well as the presence of hydrogen halides, may lead to the re-alumination of the zeolite. The presence of aluminium in the binder would also tend to reduce the olefins selectivity of the catalyst and to reduce the stability of the catalyst over time.

The binder is present in a content of at least 10 wt. % as based on the total weight of the first catalytical composition; preferably in a content of at least 20 wt. %, most preferably in a content of 30 wt. %, even more preferably in a content of at least 40 wt. %, and most preferably in a content of at least 50 wt. %.

Non-limiting examples of silicon sources suitable for the binder of the catalytical composition include silicates, precipitated silicas, for example, Zeosil® available from Rhodia, fumed silicas, for example, Aerosil®200 available from Degussa Inc., New York, N.Y., silicon compounds such as tetraalkyl orthosilicates, for example, tetramethyl orthosilicate (TMOS) and tetraethylorthosilicate (TEOS), colloidal silicas or aqueous suspensions thereof, for example Ludox® HS-40 available from E.I. du Pont de Nemours, Wilmington, Del., silicic acid, alkali-metal silicate, or any combination thereof.

Other suitable forms of amorphous silica include silica powders, such as Ultrasil® VN3 SP (commercially available from Degussa).

Other non-limiting examples of a suitable solid silica source are special granulated hydrophilic fumed silica, mesoporous silica and high surface area precipitated silica SIPERNAT® from Evonik, Hi-Sil 233 EP (available from PPG Industries) and Tokusil (available from Tokuyama Asia Pacific).

Also, suitable amorphous silica sources include silica sols, which are stable colloidal dispersions of amorphous silica particles in an aqueous or organic liquid medium, preferably water.

Non-limiting examples of commercially available silica sols include those sold under the tradenames Nyacol® (available from Nyacol Nano Technologies, Inc. or PQ Corp.), Nalco (available from Nalco Chemical Company), Ultra-Sol (available from RESI Inc), Ludox® (available from W.R. Grace Davison), NexSil™ (available from NNTI).

Many silica sols are prepared from sodium silicate and inevitably contain sodium. It is, however, found that the presence of sodium ions can cause sintering of the silica body at high temperature and/or affect catalytic performance. Therefore, if silica sols containing sodium are used, a step of ion exchange may be required to reduce or remove sodium. To avoid carrying out ion exchange steps, it is convenient to use silica sols that contain very little or, ideally, no detectable traces of sodium and have a pH value of less than 7. Most preferably, the silica sol used in the process is slightly acidic with or without polymeric stabilizers. Non-limiting examples of silica sols that contain no detectable traces of sodium include Bindzil® 2034D1, Levasil® 200, Nalco 1034A, Ultra-Sol 7H or NexSil™ 20A.

In some case, silica dispersion prepared with alkylammonium might be useful. Non-limiting examples of commercially low sodium silica sols stabilized by ammonia or alkylammonium cations include LUDOX® TMA (available from W.R. Grace Davison) or VP WR 8520 from Evonik.

The silica sols with higher $SiO_2$ content than 30 wt. % and even up to 50 wt. %, for example, W1250, W1836, WK341, WK7330 from Evonik are particularly preferred.

The preferred source of silicon is a silica sol or a combination of silica sol with precipitated or fumed silica.

Sub-Step (ii): Putting into Contact the Fourth Stream 27 with the First Catalytical Composition The homologation reaction is carried out under first reaction conditions.

Said first reaction conditions comprise a temperature ranging between 250° C. and 460° C., preferably between 280° C. and 420° C., more preferably between 280° C. and 400° C. Said first reaction conditions also comprises a pressure ranging between 0.2 MPa and 1.5 MPa, preferably between 0.4 MPa and 1.0 MPa; more preferably between 0.5 MPa and 1.0 MPa.

The weight of feed comprising flowing per unit of weight of the catalyst per hour (weight hourly space velocity, WHSV) is comprised between $0.1\ h^{-1}$ and $100\ h^{-1}$, preferentially between $1.0\ h^{-1}$ and $15\ h^{-1}$. More preferably, WHSV is comprised between $1.5\ h^{-1}$ and $10\ h^{-1}$. Even more preferably, WHSV is comprised between $2.0\ h^{-1}$ and $6.0\ h^{-1}$. This means that the homologation catalyst of the present disclosure can convert the weight of the fourth stream 27 that is superior to the amount of the catalyst present in the homologation reactor 31.

Exiting the homologation reactor 31, a first product stream 33 of C1-C7 hydrocarbons, including olefins, paraffins and aromatics, can be recovered. Alkyl bromide and hydrogen bromide are also comprised in the first product stream 33.

A sub-step of separation the C2-C4 hydrocarbons from said first product stream 33 can be carried out to form a C2-C4 stream. Said C2-C4 stream can be further separated into an ethylene stream and/or into a propylene stream. In the preferred example of the present disclosure, the first product stream 33 can be further processed under a cracking sub-step (iii).

Optional Sub-Step (iii): Cracking

The first product stream 33 is then conveyed into a cracking reactor 37, possibly via one or more heat exchanger 35 arranged between the homologation reactor 31 and the cracking reactor 37 so that one or more steps of adjusting the temperature of the first product stream 33 can be performed. For example, the cracking reactor 37 can be selected from a fixed bed reactor or a fluidized bed reactor, preferably a fixed bed reactor.

The cracking reactor 37 is loaded with a second catalytical composition comprising at least one cracking catalyst.

For example, said cracking catalyst is a catalyst suitable for an olefin cracking reaction. Preferred catalysts for the olefin cracking reaction can be selected from one or more zeolites and/or one or more clays.

With preference, said cracking catalyst comprises one or more zeolites selected from silicalites from the MFI family, crystalline silicate from the MFI family with a Si/Al atomic ratio of at least 180, crystalline silicate from the MEL family with a Si/Al atomic ratio ranging between 150 and 800, and/or phosphorous-modified zeolite from the MFI, MEL, FER, MOR family and/or phosphorous-modified clinoptilolite.

In one embodiment, said cracking catalyst comprises one or more zeolites selected from silicalites from the MFI family, optionally with a silica binder.

Examples of suitable catalysts were disclosed in the international patent application published WO2004/048299.

Examples of crystalline silicate from the MFI family are ZSM-5 and silicalite. An example of crystalline silicate from the MEL family is ZSM-11, which is known in the art. Other suitable non-limiting examples are boralite D and silicalite-2, or any mixtures thereof.

The preferred crystalline silicates have pores or channels defined by ten oxygen rings and a high Si/Al atomic ratio. The catalyst having a high Si/Al atomic ratio may be manufactured by removing aluminium from a commercially available catalyst. The commercially available catalysts may be modified by steaming to remove at least part of inter-framework aluminium followed by leaching step to remove external aluminium.

The cracking catalyst can be formulated with a binder, preferably an inorganic binder, and shaped to the desired shape, e.g. extruded pellets. The binder is an inorganic material selected from clays, silica, metal oxides. Preferably, the binder content ranges from 5 to 50% by weight, more typically from 15 to 35% by weight, based on the weight of the cracking catalyst. More preferably, the binder is a silica binder.

The cracking catalyst can be subjected to a steaming step before sub step (iii).

The olefin cracking reaction is known per se. It has been described in EP1035915, EP1036133, EP1036134, EP1036135, EP1036136, EP1036137, EP1036138, EP1036139, EP1190015, EP1194500, EP1194502, and EP1363983; the content of which is incorporated in the present description.

For example, the second reaction conditions comprise a temperature ranging from 400° C. to 600° C., preferably ranging from 450° C. to 550° C.; and/or a weight hourly space velocity comprised between 0.1 h$^{-1}$ and 100 h$^{-1}$, preferably comprised between 1.5 h$^{-1}$ and 10 h$^{-1}$; and/or a pressure ranging between 0.5 MPa and 1.5 MPa, preferentially between 0.6 MPa and 1.0 MPa.

The stream exiting the cracking reactor 37 is a second product stream 39 comprising C1-C8 hydrocarbons and hydrogen bromide, in particular comprising unreacted methane, C2-C4 olefins, C2-C8 paraffins, C6-C8 aromatics, hydrogen bromide, alkyl bromides including monobromomethane.

A sub-step of separation the C2-C4 hydrocarbons from said second product stream 39 can be carried out to form a C2-C4 stream (17, 83). Said C2-C4 stream (17, 83) can be further separated into an ethylene stream 91 and/or into a propylene stream 99.

Removal of Hydrogen Bromide and Further Recycling Thereof

When the conversion unit 113 comprises a cracking reactor 37, the second product stream 39 is conveyed into a physical separation unit 115. This is the preferred configuration, shown in any of the FIGS. 1 to 3. Alternatively, when the conversion unit 113 does not comprise the cracking reactor, this is the first product stream 33 that is conveyed into the physical separation unit 115 (not shown).

In the physical separation unit 115, the second product stream 39 can then be directed into one or more separation column (43, 59, 65, 123, 129). For example, the second product stream 39 is cooled down in one or more heat exchangers 41 before being processed in a first separation column, being a debutanizer 43. For example, the debutanizer 43 is a distillation column and/or is working at a temperature ranging between 50° C. and 70° C., and/or is working at a pressure ranging between 0.3 MPa to 1.0 MPa. Passing the product stream 39 in the debutanizer 43 separates the product stream 39 into a fifth stream (51, 55) and a sixth stream (45, 49), the fifth stream (51, 55) comprising C1-C4 hydrocarbons and hydrogen bromide and the sixth stream (45, 49) comprising C5-C8 hydrocarbons, aromatics (i.e., at least one of benzene, toluene and/or xylene) and hydrogen bromide.

An optional separation step can be provided on the sixth stream 45, through for example a separator 47, such as an adsorption column, to remove hydrogen bromide and recover a stream of a C5-C8 hydrocarbons stream and aromatics (i.e., at least one of benzene, toluene and/or xylene), i.e. a gasoline stream 49. A stream 167 of hydrogen bromide can also be recovered. As indicated on FIG. 1, the gasoline stream 49 can be further conveyed into one or more distillation columns 161 to separate a C5-C6 hydrocarbons stream 163 that can be further recycled back to the homologation reactor 31. For example, the distillation column 161 is a dehexanizer. For example, the pressure conditions implemented in the one or more distillation columns 161 are comprised between 0.1 MPa and 0.4 MPa, preferably between 0.2 MPa and 0.3 MPa. For example, the temperature conditions implemented in the one or more distillation columns 161 are comprised between 50° C. and 150° C., preferably between 55° C. and 145° C. The remaining part of the gasoline stream 49, namely a stream 165 comprising aromatics (i.e., at least one of benzene, toluene and/or xylene) and C7-C8 hydrocarbons can be optionally further separated into a C7-C8 hydrocarbons stream and an aromatics stream (not shown).

The C5-C6 hydrocarbons stream 163 can be purged, to recover a fuel gas stream 169 comprising C5-C6 hydrocarbons.

The separation and recycling of the C5-C6 hydrocarbons stream 163 back to the homologation reactor 31 allows to the first catalytical composition to convert the fourth stream 27 comprising unreacted methane, methyl bromide and hydrogen bromide into a first product stream 33 comprising C1-C7 hydrocarbons and hydrogen bromide. The continuous feeding of C5-C6 hydrocarbons to the homologation reactor 31 allows their reaction with methyl bromide to generate C6-C7 hydrocarbons and therefore form the first product stream 33 comprising C1-C7 hydrocarbons.

Although only shown in the installation illustrated on FIG. 1, the separation and recycling of the C5-C6 hydrocarbons stream 163 back to the homologation reaction 31, along with the optional purge of the C5-C6 hydrocarbons stream 163 to recover a fuel gas stream 169 comprising C5-C6 hydrocarbons can be advantageously implemented on the installation of FIGS. 2 and 3 so that the first product stream 33 comprises C1-C7 hydrocarbons.

The fifth stream 51 can be submitted to one or more further separation steps such as a step of separation of hydrogen bromide from the C1-C4 hydrocarbons.

First Embodiment

As shown in FIG. 1, this step can be performed in an extractive distillation system, comprising one or more separation columns (59, 65). In this case, the removal of hydrogen bromide is performed by non-aqueous extraction. For example, the fifth stream 51 comprising C1-C4 hydrocarbons and hydrogen bromide is passed through one extractive distillation column 59, which is loaded with one specific solvent, such as solvent comprising alcohol, carboxylic acid, ketone, organobromine compounds, ionic liquid, organic acid anhydride and/or nitrile. For example, one suitable solvent is acetic acid. The hydrogen bromide which is contained in the fifth stream 51 is thus absorbed on said specific solvent, which allows the separation of the C1-C4 hydrocarbons and then the production of a stream 61 comprising C1-C4 hydrocarbons. Said stream 61 comprising C1-C4 hydrocarbons can be recycled into the first stream (1, 5) comprising natural gas and/or into the one or more of the reactors 19 of the bromination unit 111. In a preferred example of the present disclosure, the stream 61 comprising C1-C4 hydrocarbons is conveyed into the products-recovery unit 119 (see below).

The installation 1, and in particular the physical separation unit 115, may also comprise one or more water adsorbers, such as the water adsorption column 53, arranged between the debutanizer 43 and the extractive distillation system so that one or more steps of drying the fifth stream 51 before it enters the extractive distillation system is included.

Once the separation of the C1-C4 hydrocarbons has occurred, the remaining stream 63 exiting the extractive distillation column 59 is directed to a second separation column 65 of the extractive distillation system to recover the solvent which was used in the extractive distillation column 59 and to produce a hydrogen bromide-rich stream 69. Said second separation column 65 is preferably a distillation column. The extractive distillation system as described provides the advantage that the hydrogen bromide-rich stream 69 does not comprise water. The recovered solvent 67 is preferably redirected to the extractive distillation column 59 so that the generation of the hydrogen bromide-rich stream 69 can be continuously achieved.

With preference, the hydrogen bromide-rich stream 69 comprises only hydrogen bromide.

The additional step (g) of the process, which can advantageously be carried out in the case where the optional step (f) of separating hydrogen bromide from the third stream 21 has been performed, is an oxidation step which is carried out by electrolysis.

Thus, the hydrogen bromide-rich stream 69, exiting the physical separation unit 115, is conveyed to an electrolysis unit 117 to produce a stream 77 comprising hydrogen and a stream 79 which is a bromine-rich stream. More particularly, the hydrogen bromide-rich stream 69 can be directed in an electrolysis cell, being preferentially a gas-phase electrolysis cell 73. The gas-phase electrolysis cell 73 can be a proton exchange membrane reactor and is supplied with an energy stream 75, consisting preferentially of non-fossil renewable energy (i.e. green electricity coming from solar energy and/or wind energy).

As the hydrogen bromide-rich stream 69 may comprise only hydrogen bromide, its electrolysis in the electrolysis unit 117 under gaseous phase provide a bromine-rich stream 79 that comprises only bromine and can be thus put in contact without any further treatment with the methane stream 15.

Second Embodiment

As shown on FIG. 2, as an alternative to the first embodiment, the fifth stream 51 comprising C1-C4 hydrocarbons and hydrogen bromide, is directed through one extractive distillation column 59, which is loaded with one specific solvent, such as solvent comprising alcohol, carboxylic acid, ketone, organobromine compounds, ionic liquid, organic acid anhydride and/or nitrile. For example, one suitable solvent is acetic acid. The hydrogen bromide which is contained in the fifth stream 51 is thus absorbed on said specific solvent, which allows the separation of the C1-C4 hydrocarbons and then the production of a stream 61 comprising C1-C4 hydrocarbons. Said stream 61 comprising C1-C4 hydrocarbons can be recycled into the first stream (1, 5) comprising natural gas and/or into the one or more of the reactors 19 of the bromination unit 111. In a preferred example of this second embodiment, the stream 61 is conveyed into the products-recovery unit 119 (see below).

The installation 1, and in particular the physical separation unit 115, may also comprise one or more water adsorbers, such as the water adsorption column 53, arranged between the debutanizer 43 and the extractive distillation column 59 so that one or more steps of drying the fifth stream 51 before it enters the extractive distillation column 59 is included.

Once the separation of the C1-C4 hydrocarbons has occurred, the remaining stream 72, comprising hydrogen bromide and the specific solvent that was used in the extractive distillation column 59, is directed to one electrolysis unit 117 to produce a steam 77 comprising hydrogen and a stream 64 comprising bromine, unconverted hydrogen bromide and said specific solvent.

More particularly, the remaining stream 72 is directed in an electrolysis cell, being preferentially a liquid-phase electrolysis cell 76. The liquid-phase electrolysis cell 76 is supplied with an energy stream 75, comprising preferentially non-fossil renewable energy (i.e. green electricity coming from solar energy and/or wind energy).

The stream 64 exiting the electrolysis unit 117 is then conveyed into a separation column 65 to recover the solvent which was used in the extractive distillation column 59, and to produce a bromine-rich stream 79. The unconverted hydrogen bromide being absorbed on said specific solvent, it is possible to separate the bromine and form a bromine stream 79. The recovered stream 67 which comprises a mixture of said specific solvent and hydrogen bromide is preferably redirected to the extractive distillation column 59 so that the generation of the bromine stream 79 can be continuously achieved.

Also, to remove any traces of hydrogen bromide in the bromine stream 79, it is possible to convey the stream 79 into a decanter (not shown) to remove further traces of hydrogen bromide from the bromine stream 79. before being put into contact with the methane stream 15 before entering into the bromination reactor 19 or before being redirected into the bromination unit 111.

Third Example

As shown on FIG. 3, the fifth stream 51 comprising C1-C4 hydrocarbons and hydrogen bromide is passed through a water stripper column 123, in which the hydrogen bromide is stripped/exchanged against water. For example, the water stripper column 123 is a column with a packed bed composed of Raschig ring. This leads to the formation of a hydrogen bromide stream 135 also comprising water that is expulsed out of the physical separation unit 115. The water stripper column 123 thus allows the separation of a C1-C4 hydrocarbons stream 125, which, optionally after a step of adjusting its temperature in one or more heat exchangers 127, enters into a decantation system 129 to remove the water. A water stream 131 exiting the decantation system 129 is reintroduced into the water stripper column 123 to further removed hydrogen bromide from the fifth stream 51. Upon decantation of water, a stream 61 comprising C1-C4 hydrocarbons is obtained.

Similarly to the embodiment where the removal of hydrogen bromide is conducted in presence of a non-aqueous solvent, said stream 61 comprising C1-C4 hydrocarbons can be recycled into the first stream (1, 5) comprising natural gas and/or into the one or more of the reactors 19 of the bromination unit 111. In a preferred example of the present disclosure, the stream 61 comprising C1-C4 is conveyed into the products-recovery unit 119 (see below).

The installation 1, and in particular the physical separation unit 115, may also comprise one or more heat exchangers 57 arranged between the debutanizer 43 and the extractive distillation system (FIG. 1) or the water stripper column 123 (FIG. 2) so that one or more steps of adjusting the temperature of the fifth stream 51 before it enters the extractive distillation system or the water stripper column 123 is included.

The hydrogen bromide stream 135 comprising water, exiting the physical separation unit 115, is then conveyed to an electrolysis unit 117 to produce a stream 77 comprising hydrogen and a stream 141 comprising aqueous bromine and unconverted hydrogen bromide. The hydrogen stream 77, before being recovered, can be optionally dried in a drier system 139. For example, the drier system 139 is a desiccant. For example, the desiccant can be a molecular sieve, such as one or more zeolite from the LTA family. Among the LTA family, zeolites from LTA-3A, LTA-4A and/or LTA-5A can be selected. In another example, the drier system 139 is a hydrogen drying system as described in US2016/0129390. For example, the drier system 139 works under room temperature, such as between 15° C. and 25° C., and/or under pressure conditions of at least 0.1 MPa, preferably ranging between 0.1 MPa and 2.0 MPa, more preferably ranging between 0.5 MPa and 1.5 MPa, even more preferably ranging from 0.6 MPa to 1.0 MPa.

The stream 141 comprising aqueous bromine and unconverted hydrogen bromide also comprises hydrogen bromide that is generated due to the hydrolysis of bromine into the water. The stream 141 can then be conveyed in a bromine-recovery unit 159, and more particularly into a washing tower 143 included in said bromine-recovery unit 159. The washing tower 143 allows the separation of a hydrogen bromide stream 153 that can be optionally recycled into the water stripper column 123 of the physical separation unit 115. Also exiting from the washing tower 143, a stream 145 comprising aqueous bromine and possibly traces of hydrogen bromide is directed to an optional decantation system 149 in which the hydrogen bromide is further separated into a hydrogen bromide stream 151 and optionally recycled into the washing tower 143. The bromine stream 155 exiting the optional decantation system 149 is dried in a dryer system 157 to produce the bromine stream 79 that exits the bromine-recovery unit 159 and that can be optionally put into contact with the methane stream 15 before being redirected into the bromination reactor 19 or reused in the bromination unit 111. For example, the dryer system 157 is a desiccant. For example, the desiccant can be a molecular sieve, such as one or more zeolite from the LTA family. Among the LTA family, zeolites from LTA-3A, LTA-4A and/or LTA-5A can be selected.

Electrolysis of Hydrogen Bromide in the Electrolysis Unit 117

The following two half-reactions occurring in the electrolysis unit 117 of any of the described embodiments can be summarized as follows:

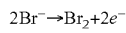
$$2Br^- \rightarrow Br_2 + 2e^-$$

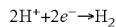
$$2H^+ + 2e^- \rightarrow H_2$$

For example, the electrolysis can be achieved in a proton-exchange membrane electrolysis cell. When such kind of electrochemical cells is used, it may comprise an anode side and a cathode side, the anode side and the cathode side is separated by a proton-conducting membrane, for example, a proton-conducting membrane made in ceramic materials.

For example, when the step (g) of electrolysis is carried out in gas phase, the step (g) of electrolysis is performed under temperature conditions ranging between 300° C. and 700° C., preferably between 325° C. and 675° C., more preferably between 375° C. and 625° C. For example, when the step (g) of electrolysis is carried out in liquid phase including the aqueous phase, the step (g) of electrolysis is performed under temperature conditions ranging between 20° C. and 80° C., preferably between 25° C. and 70° C., more preferably between 30° C. and 40° C. For example, whichever the phase in which the step (g) of electrolysis is carried out, the step (g) of electrolysis is performed under pressure conditions of at least 0.1 MPa, preferably ranging between 0.1 MPa and 2.0 MPa, more preferably ranging between 0.5 MPa and 1.5 MPa, even more preferably ranging from 0.6 MPa to 1.0 MPa.

Knowing the potential difference for hydrogen bromide electrolysis of −1.07 V, the system requires the theoretical minimal energy supply of 206 kJ/mol. This means that to recover one ton of bromine, the electrolysis cell theoretically needs 358 kWh for 100% hydrogen bromide conversion and assuming 100% energy efficiency.

The regenerated bromine-rich stream 79 exiting from the electrolysis unit 117 can be preferentially used in the bromination unit 111, either by being mixed with the methane stream 15 before entering the bromination unit 111 or by being directly conveyed into the bromination reactor 19. When the process comprises this recycling step, there is no net consumption of bromine, because it is fully regenerated in the process.

The most preferred way to carry out the electrolysis step is to do it under gaseous phase, with preference in the absence of water, since the bromine-rich stream 79 only comprises bromine and the installation of FIG. 1 does not need to have a bromine-recovery unit disposed downstream of the electrolysis unit 117. The electrolysis of hydrogen bromine-rich stream 69 allows the formation of hydrogen 77 as a pure stream product and avoids the use of oxidative bromine recovery routes. This is advantageous in the sense it prevents the consumption of oxygen coming from air separation units that are cumbersome technique. Besides, the use of bromine recovery by electrolysis carried out in gaseous phase allows preventing the generation of water contaminated with bromine as end-products, which occurs when oxidative bromine recovery routes are used. Therefore, the subsequent treatment of water is not necessary.

When the electrolysis is performed in liquid phase (as in the installation of FIG. 2), or more particularly in aqueous phase (as in the installation of FIG. 3), the electrolysis does not fully convert hydrogen bromide into bromine. For example, when the electrolysis is performed in aqueous phase, stable performances of the electrolysis unit 117 are achieved to obtain up to about 60% of hydrogen bromide conversion along with an energy efficiency of about 85%. However, the presence of at least one bromine-recovery unit 159 may allow recovering a bromine-rich stream 79 comprising only bromine.

Recovery of Valuable Chemicals Such as Ethylene and/or Propylene

The installation for carrying out the present process further comprises one products-recovery unit 119 downstream of the demethanizer 13 of the pre-treatment unit 121. This is the most preferred configuration. Alternatively, a demethanizer other than the demethanizer 13 of the pre-treatment unit 121 can be installed upstream of the products-recovery unit 119.

The product-recovery unit 119 is supplied with the C2-C4 hydrocarbons stream 17 separated from the first stream (1, 5, 11), but also, possibly by the stream 61 comprising C1-C4 hydrocarbons coming from the dibromomethane and hydrogen bromide separation unit 111 which has been processed to a demethanizer, preferably the demethanizer 13 of the pre-treatment unit 117. The use of the demethanizer 13 of the pre-treatment unit 117 allows maximizing the potential of the component of the installation, rendering the installation cost-effective.

The C2-C4 hydrocarbons stream 17 can be optionally conveyed into one or more heat exchangers 81 to adjust the temperature of the C2-C4 hydrocarbons stream 83 before it enters into a de-ethanizer 85. For example, the de-ethanizer 85 can be a cryogenic distillation column. With preference, the de-ethanizer 85 works under a temperature ranging between −5° C. and 15° C., more preferably between 0° C.

and 10° C., and/or under a pressure ranging between 1.5 MPa and 2.5 MPa. Upon passage of the C2-C4 hydrocarbons stream (17, 83) within said de-ethanizer 85, a C2 hydrocarbons stream 87 and a C3-C4 hydrocarbons stream 95 are generated.

Said C2 hydrocarbons stream 87 is conveyed to at least one C2 splitter 89. For example, one or more C2 splitters are one or more cryogenic distillation columns. For example, the one or more C2 splitters work under a temperature ranging between −40° C. and −20° C., more preferably between −35° C. and −25° C., and/or under a pressure ranging between 1.5 MPa and 2.5 MPa, preferably between 1.7 MPa and 2.3 MPa. This allows to remove the ethane from the C2 hydrocarbons stream 87 to recover an ethylene stream 91 and optionally an ethane stream 93.

Said C3-C4 hydrocarbons stream 95 is conveyed to at least one C3 splitter 97. For example, one or more C3 splitters are one or more cryogenic distillation columns. For example, the one or more C3 splitters work under a temperature ranging between 20° C. and 60° C., more preferably between 30° C. and 50° C., and/or under a pressure ranging between 1.5 MPa and 2.5 MPa, preferably between 1.7 MPa and 2.3 MPa. This allows recovering a propylene stream 99 and a liquid petroleum gas (LPG) stream 101.

Test and Determination Methods

Figure 5:
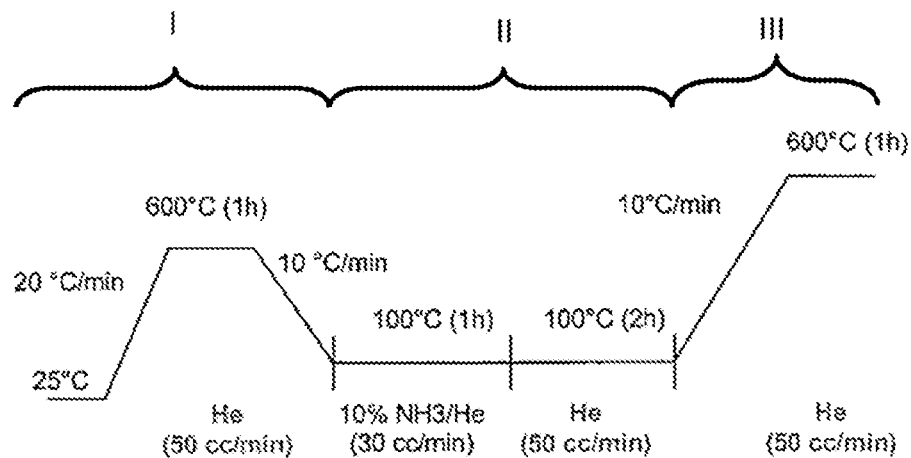
FIG. 5 shows an example of the settings of the temperature-programmed desorption (TPD) method.

Temperature Programmed Desorption (TPD) is the method of observing desorbed molecules from a surface when the surface temperature is increased. It has been performed by following the heating sequences I, II and III shows on FIG. 5, respectively corresponding to activation, saturation and analysis. In brief, in the first step (marked as I on FIG. 5), starting from room temperature (25° C.) under a flow of helium (rate 50 cc/min), the temperature has been gradually increased to 600° C. at a rate of 20° C./min. After 1 hour at 600° C., the zeolite sample is considered as being activated and the temperature is then gradually decreased to 100° C. at a rate of 10° C./min. Then, in the second step (marked as II on FIG. 5) during 3 hours, the temperature is maintained at 100° C. and in the first 1 hour, 10% of ammonia ($NH_3$) is added to the helium flow (which is decreased to 30 cc/min). The surface of the zeolite is thus saturated with the molecules of ammonia that are going to be adsorbed onto the surface. The last 2 hours of the temperature threshold at 100° C., the initial flow of helium is reinstated. Then, in the third step (marked as III in FIG. 5) the temperature is increased again to 600° C. at a rate of 10° C./min to desorb the ammonia. The sample is maintained at 600° C. for an additional one hour. It is highlighted that the skilled person could use different parameters (time, temperature, flow rate, carrier gas) to perform the method. The measurement of the content of ammonia using a thermal conductivity detector allows to recognize the different adsorption conditions of the ammonia onto the zeolite and allows for obtaining a description of the surface of the zeolite, such as the number of acid sites.

Gas chromatography experiments were carried out to determine quantitatively the selectivity of the reaction. It was performed on a silica BOND column (60 m×0.32 mm) using Agilent operated by ChemStation software.

Example

The advantages of the present disclosure are illustrated by the following examples. However, it is understood that the disclosure is no means limited to the specific examples.

A pilot line simulating the process has been constructed. The homologation reactor 31 and cracking reactor 37 were charged with a silicalite catalyst from the MFI family having a Si/Al molar ratio of >800 (as defined by TPD) and shaped with a $SiO_2$ binder. For the catalytic test, the catalyst was pressed, then crushed and seized between 35-45 mesh screens and preactivated in an $N_2$ flow at 525° C. for 6 h. Said homologation reactor 31 and cracking reactor 37 are fixed-bed tubular reactors with inner diameter of 11 mm made of INCONEL alloy. The homologation reactor 31 had a catalyst loading ~10 mL (6 g) and the cracking reactor 37 was ~3.5 mL (2 g).

After preactivation the temperature in homologation reactor 31 was changed to 300° C. and in cracking reactor 37—to 550° C. Pure $N_2$ flow was replaced with the flow of $N_2/CH_3Br$ 7/3 mol. with WHSV of $CH_3Br$/catalyst of 3 $h^{-1}$ (~18 $gh^{-1}$). The reactor pressure was around 6 bara (0.6 MPa) during the test run in both reactors and was controlled by Equilibar back-pressure controllers.

The sampling was done from a 2-way split valve installed in between the homologation reactor and the cracking reactor and from the effluent of the cracking reactor.

Table 1 shows the molar composition of the first product stream 33 of C1-C7 hydrocarbons exiting the homologation reactor 31 and of the second product stream 39 comprising C1-C8 hydrocarbons exiting the cracking reactor 37.

TABLE 1

Molar composition of first product stream 33 and second product stream 39.

| Product | Molar composition (%) of first product stream 33* | Molar composition (%) of second product stream 39* |
|---|---|---|
| C1 | 1 | 1 |
| C2 | 0 | 1 |
| C2= (ethylene) | 3 | 14 |
| C3 | 1 | 3 |
| C3= (propylene) | 13 | 57 |
| C4 | 7 | 8 |
| C4= | 34 | 0 |
| C5 | 4 | 5 |
| C5= | 13 | 0 |
| C6 | 3 | 3 |
| C6= | 9 | 0 |
| C7 | 1 | 1 |
| C7= | 2 | 0 |
| C8 | 0 | 1 |
| Heavy and dienes | 7 | 0 |
| Alkyl bromides | 1 | 0 |
| Aromatics | 1 | 5 |
| Total amount of olefins | 74 | 71 |
| Total amount of C2-C3 olefins | 16 | 71 |
| Total amount of paraffins | 17 | 23 |

*The molar composition has been determined by gas chromatography analysis.

From the results displayed in table 1, it can be observed that when the optional cracking sub-step (iii) is carried out, the content ethylene and propylene increases in the second product stream 39. Therefore, upon subsequent sub-step (iv) of separation, the production of these valuable chemicals in the installation of the present disclosure can be greatly improved compared to an installation devoid of a cracking reactor. Thanks to the configuration of the installation of the present disclosure, in addition to favour the production of ethylene and propylene, the separation of dibromomethane protects the catalysts from coke contamination and the recovered dibromomethane is not wasted but can be transformed into carbon, notably graphite and carbon black which can be used as reinforcing filler in rubber product or as a colour pigment. Also, using the present installation, the recycling of the bromine used for activation of methane allows the productions of hydrogen.

Table 2 shows the production of the installation simulated by ASPEN PLUS V9 software.

TABLE 2

Production of the described installation

|  | Compounds | Reference number in FIG. 1 | Flux (ton/hour) |
|---|---|---|---|
| REACTANTS | Natural gas | first stream 1 | 165 |
|  | Bromine | second stream 79 | 38 |
| PRODUCTS | Hydrogen | hydrogen stream 77 | 71 |
|  | C1 purge stream and C5-C6 purge stream | fuel gas stream 9 comprising methane and fuel gas stream 169 comprising C5-C6 | 14 |
|  | Ethylene | ethylene stream 91 | 8 |
|  | Ethane | ethane stream 93 | 1 |
|  | Propylene | propylene stream 99 | 78 |
|  | LPG | LPG stream 101 | 6 |
|  | Aromatics | in 165 | 13 |
|  | Heavy paraffins | In 165 | 6 |
|  | hydrogen bromide | hydrogen bromide stream 167 exiting the separator 47 | <0.1 |
|  | Dibromomethane | Dibromomethane stream 103 | 56 |

The fluxes of the products displayed on table 2 show the potential of the installation of the present disclosure.

The invention claimed is:

1. A process for converting a stream comprising methane into chemicals, said process being characterized in that it comprises the following steps:
   a) providing a first stream comprising methane;
   b) providing a second stream which is a bromine-rich stream;
   c) putting into contact said first stream with said second stream under bromination reaction conditions to obtain a third stream comprising at least unreacted methane, methyl bromide, dibromomethane, and hydrogen bromide;
   d) removing said dibromomethane from said third stream under separation conditions, to produce a dibromomethane stream and a fourth stream comprising unreacted methane, methyl bromide and hydrogen bromide;
   e) converting the fourth stream into chemicals;
   f) separating hydrogen bromide from said third stream and/or said fourth stream, to provide a hydrogen bromide-rich stream; wherein the step of separating hydrogen bromide is performed by non-aqueous extraction;
   g) subjecting the hydrogen bromide-rich stream of step (f) to an electrolysis step (g) to produce a hydrogen stream and/or a bromine stream, said bromine stream being optionally reused in step (c).

2. The process according to claim 1, characterized in that the separation conditions of step (d) comprise temperature conditions of at most 150° C. and/or pressure conditions ranging between 0.1 MPa and 1.0 MPa.

3. The process according to claim 1, characterized in that said electrolysis step (g) is carried out under gaseous phase or liquid phase.

4. The process according to claim 1, characterized in that said electrolysis is performed under water-free conditions.

5. The process according to claim 1, characterized in that the dibromomethane stream of step (d) is further converted into carbon by performing carbonization of said dibromomethane stream, said carbonization is carried out:
   using electrical energy input; and/or
   at a temperature ranging between 600° C. and 3000° C.

6. The process according to claim 1, characterized in step (e) of conversion of the fourth stream into chemicals comprises the following sub-steps:
   i. providing a first catalytical composition comprising at least one homologation catalyst,
   ii. putting into contact said fourth stream with the first catalytical composition under first reaction conditions to provide a first product stream comprising C1-C7 hydrocarbons and hydrogen bromide;
   iii. optionally, providing a second catalytical composition comprising at least one cracking catalyst and putting into contact said first product stream with the second catalytical composition under second reaction conditions, to provide a second product stream comprising C1-C8 hydrocarbons and HBr;
   iv. separating C2-C4 hydrocarbons from said first product stream and/or from said second product stream when sub-step (iii) is carried out, to form a C2-C4 stream.

7. The process according to claim 6, characterized in that said C2-C4 stream is further separated into an ethylene stream and/or into a propylene stream.

8. The process according to claim 6, characterized in that the first catalytical composition is steamed before sub-step (ii) and the one or more homologation catalysts of the first catalytical composition comprise one or more zeolites and a binder, wherein said one or more zeolites comprise at least one 10-membered ring channel.

9. The process according to claim 6, characterized in that the first reaction conditions comprise one or more of a temperature ranging between 250° C. and 460° C., a pressure ranging between 0.5 MPa and 1.0 MPa, and a weight hourly space velocity comprised between 0.1 $h^{-1}$ and 100 $h^{-1}$.

10. The process according to claim 6, wherein sub-step (iii) is carried out, said process being characterized in that said at least one cracking catalyst comprises one or more zeolites and/or one or more clays.

11. The process according to claim 10, characterized in that said at least one cracking catalyst comprises one or more zeolites selected from silicalites from the MFI family, crystalline silicate from the MFI family with a Si/Al atomic ratio of at least 180, crystalline silicate from the MEL family with a Si/Al atomic ratio ranging between 150 and 800, and/or phosphorous-modified zeolite from the MFI, MEL, FER, or MOR family.

12. The process according to claim 6, wherein sub-step (iii) is carried out, characterized in that the second reaction conditions comprise one or more of a reaction temperature ranging from 400° C. to 600° C., a pressure ranging between 0.4 MPa and 1.0 MPa, and a weight hourly space velocity comprised between 0.1 $h^{-1}$ and 100 $h^{-1}$.

13. The process according to claim 6, characterized in that the step (e) of conversion of the fourth stream into chemicals further comprises the sub-step (v) of separating an unreacted methane stream from said first product stream and/or from said second product stream when sub-step (iii) is carried out, to form a methane stream.

14. The process according to claim 13, characterized in that said methane stream is recycled in the first stream of step (a).

15. The process according to claim 13, characterized in that said methane stream is purged to form a fuel gas stream.

16. The process according to claim 1, characterized in that the bromination reaction conditions of step (c) include one or more of a temperature ranging from 300° C. to 500° C.

in the absence of a catalyst, a pressure ranging from 0.1 MPa to 2.0 MPa, and a molar ratio methane to bromine of at least 2.5:1.

17. The process according to claim 1, characterized in that the step (a) of providing a first stream comprising methane comprises providing a natural gas comprising methane at a content of at least 75 mol. % of the total molar content of said natural gas.

18. The process according to claim 1, characterized in that the step (a) of providing a first stream comprising methane comprises providing a natural gas and purifying the natural gas to remove one or more selected from sulphur, nitrogen, water, oxygen and carbon dioxide.

\* \* \* \* \*